(12) United States Patent
Ryan et al.

(10) Patent No.: US 7,824,709 B2
(45) Date of Patent: Nov. 2, 2010

(54) LIPOPHILIC DRUG DELIVERY VEHICLE AND METHODS OF USE THEREOF

(75) Inventors: Robert O. Ryan, El Cerrito, CA (US); Michael N. Oda, Fairfield, CA (US)

(73) Assignee: Children's Hospital and Research Center at Oakland, Oakland, CA (US)

( * ) Notice: Subject to any disclaimer, the term of this patent is extended or adjusted under 35 U.S.C. 154(b) by 1034 days.

(21) Appl. No.: 10/778,640

(22) Filed: Feb. 13, 2004

(65) Prior Publication Data

US 2004/0229794 A1 Nov. 18, 2004

Related U.S. Application Data

(60) Provisional application No. 60/508,035, filed on Oct. 1, 2003, provisional application No. 60/447,508, filed on Feb. 14, 2003.

(51) Int. Cl.
    *A61K 9/14* (2006.01)
(52) U.S. Cl. ......................... 424/489; 424/450
(58) Field of Classification Search ................ 424/489, 424/450
    See application file for complete search history.

(56) References Cited

U.S. PATENT DOCUMENTS

| | | | |
|---|---|---|---|
| 4,683,202 A | 7/1987 | Mullis | |
| 4,970,144 A | 11/1990 | Fareed et al. | |
| 5,128,318 A * | 7/1992 | Levine et al. | 514/2 |
| 5,490,981 A | 2/1996 | Chiknas | |
| 5,514,670 A | 5/1996 | Friedman et al. | |
| 5,576,016 A * | 11/1996 | Amselem et al. | 424/450 |
| 5,733,761 A | 3/1998 | Treco et al. | |
| 5,744,155 A | 4/1998 | Friedman et al. | |
| 5,746,223 A | 5/1998 | Williams | |
| 5,874,549 A | 2/1999 | Hadley | |
| 5,877,302 A * | 3/1999 | Hanson et al. | 536/23.1 |
| 5,948,441 A | 9/1999 | Lenk et al. | |
| 6,288,040 B1 * | 9/2001 | Muller et al. | 514/21 |
| 6,458,373 B1 | 10/2002 | Lambert et al. | |
| 6,489,297 B1 | 12/2002 | Burman et al. | |
| 6,514,523 B1 * | 2/2003 | Sparks | 424/450 |
| 2001/0009670 A1 | 7/2001 | Williams | |
| 2001/0016326 A1 | 8/2001 | Giulian | |
| 2001/0016327 A1 | 8/2001 | Giulian | |
| 2001/0025026 A1 | 9/2001 | Heartlein et al. | |
| 2001/0028895 A1 | 10/2001 | Bisgaier et al. | |
| 2001/0031262 A1 | 10/2001 | Caplan et al. | |
| 2001/0031740 A1 | 10/2001 | Unger et al. | |
| 2001/0038845 A1 | 11/2001 | Williams | |
| 2001/0038851 A1 * | 11/2001 | Allen et al. | 424/450 |
| 2001/0052136 A1 | 12/2001 | Lee et al. | |
| 2002/0001612 A1 | 1/2002 | Papahadjopoulos et al. | |
| 2002/0015941 A1 | 2/2002 | Kim et al. | |
| 2002/0018806 A1 | 2/2002 | Agrawal et al. | |
| 2002/0022053 A1 | 2/2002 | Williams | |
| 2002/0035082 A1 | 3/2002 | Grinstaff et al. | |
| 2002/0035217 A1 | 3/2002 | Uhrich | |
| 2002/0041894 A1 | 4/2002 | Williams | |
| 2002/0048746 A1 | 4/2002 | Lynch et al. | |
| 2002/0051813 A1 * | 5/2002 | Boni et al. | 424/450 |
| 2002/0068070 A1 | 6/2002 | Sasaki et al. | |
| 2002/0071862 A1 | 6/2002 | Williams | |
| 2002/0156007 A1 * | 10/2002 | Graversen et al. | 514/12 |
| 2004/0053384 A1 | 3/2004 | Sligar et al. | |

FOREIGN PATENT DOCUMENTS

| | | |
|---|---|---|
| EP | 0 277 849 | 8/1988 |
| EP | 0 277 849 A1 | 8/1988 |
| JP | 2001-500886 A | 1/2001 |
| WO | WO 96/25942 | 8/1996 |
| WO | WO-02/10501 A1 | 2/2002 |
| WO | WO 02/40501 | 2/2002 |
| WO | WO 2004/050062 | 6/2004 |
| WO | WO-2004/073684 A2 | 9/2004 |
| WO | WO-2004/073684 A3 | 9/2004 |
| WO | WO-2005/039534 A1 | 5/2005 |

OTHER PUBLICATIONS

Vasanthy et al. Biochimia et Biophysics acta 1483 (2000)15-36.*
Timothy et al. I and II protein science 2003 and Iangmuir 2000, 16.*
International Journal of Pharmaceutics 117 ( 1995) 159-163. Egg and soya phospholipids—sonication and dialysis: A study on liposome characterization.*

(Continued)

*Primary Examiner*—Gollamudi S. Kishore
*Assistant Examiner*—Snigdha Maewall
(74) *Attorney, Agent, or Firm*—Morrison & Foerster LLP

(57) ABSTRACT

The invention provides compositions and methods for delivery of a bioactive agent to an individual. Delivery vehicles are provided that include a bioactive agent in disc shaped particles that include one or more lipid binding polypeptides circumscribing the perimeter of a lipid bilayer in which the bioactive agent is localized. Chimeric lipid binding polypeptides are also provided and may be used to add additional functional properties to the delivery particles.

46 Claims, 13 Drawing Sheets

OTHER PUBLICATIONS

Anonymous. (1991). "Methods and Materials: Amplification of Nucleic Acid Sequences: The Choices Multiply," *The Journal of NIH Research* 3(2):81-94.

Arnheim, N. et al. (1990). "Polymerase Chain Reaction," *Chemical and Engineering News* 68(40):36-47.

Beckstead, J.A. et al. (2003). "Structure-Function Studies of Human Apolipoprotein A-V: A Regulator of Plasma Lipid Homeostasis," *Biochemistry* 42(31):9416-9423.

Beckstead, J.A. et al. (2005). "Combined N- and C-Terminal Truncation of Human Apolipoprotein A-I Yields a Folded, Functional Central Domain," *Biochemistry* 44(11):4591-4599.

Bielicki, J.K. et al. (2002). "Apolipoprotein A-I$_{Milano}$ and Apolipoprotein A-I$_{Paris}$ Exhibit an Antioxidant Activity Distinct from That of Wild-Type Apolipoprotein A-I," *Biochemistry* 41(6):2089-2096.

Brushia, R.J. et al. (2001). "Baculovirus-Mediated Expression and Purification of Human Serum Paraoxonase 1A," *Journal of Lipid Research* 42:951-958.

Cheng, L. et al. (May 1993). "In Vivo Promoter Activity and Transgene Expression in Mammalian Somatic Tissues Evaluated by Using Particle Bombardment," *Proc. Natl. Acad. Sci. USA* 90:4455-4459.

Dettloff, M. et al. (2001). "An N-Terminal Three-Helix Fragment of the Exchangeable Insect Apolipoprotein Apolipophorin III Conserves the Lipid Binding Properties of Wild-Type Protein," *Biochemistry* 40(10):3150-3157.

Dettloff, M. et al. (2002). "Differential Lipid Binding of Truncation Mutants of *Galleria mellonella* Apolipophorin III," *Biochemistry* 41(30):9688-9695.

Fisher, C.A. et al. (1999). "Lipid Binding-Induced Conformational Changes in the N-Terminal Domain of Human Apolipoprotein E," *Journal of Lipid Research* 40:93-99.

Fisher, C.A. et al. (Oct. 27, 2000). "The Lipid-Associated Conformation of the Low Density Lipoprotein Receptor Binding Domain of Human Apolipoprotein E," *The Journal of Biological Chemistry* 275(43):33601-33606.

Forte, T.M. et al. (1999). "Targeted Disruption of the Murine Lecithin:Cholesterol Acyltransferase Gene is Associated with Reductions in Plasma Paraoxonase and Platelet-Activating Factor Acetylhydrolase Activities but not in Apolipoprotein J Concentration," *Journal of Lipid Research* 40:1276-1283.

Forte, T.M. et al. (2002). "Altered Activities of Anti-Atherogenic Enzymes LCAT, Paraoxonase, and Platelet-Activating Factor Acetylhydrolase in Atherosclerosis-Susceptible Mice," *Journal of Lipid Research* 43:477-485.

Guatelli, J.C. et al. (Mar. 1990). "Isothermal, In Vitro Amplification of Nucleic Acids by a Multienzyme Reaction Modeled After Retroviral Replication," *Proc. Natl. Acad. Sci. USA* 87:1874-1878.

International Search Report mailed on Dec. 28, 2004, for PCT Patent Application No. PCT/US2004/025412 filed Sep. 2, 2004, 3 pages.

Janoff, A.S. et al. (Aug. 1988). "Unusual Lipid Structures Selelctively Reduce the Toxicity of Amphotericin B," *Proc. Natl. Acad. Sci. USA* 85:6122-6126.

Jonas, A. (1986). "Reconsitution of High-Density Lipoproteins," Chapter 32 in *Methods in Enzymology* 128:553-582.

Kiss, R.S. et al. (1993). "Physical Properties of Apolipoprotein A-I from the Chicken, *Gallus domesticus*," *Biochemistry* 32(31):7872-7878.

Kiss, R.S. et al. (1998). "Bacterial Expression and Characterization of Chicken Apolipoprotein A-I," *Protein Expresion and Purification* 12:353-360.

Kiss, R.S. et al. (1999). "Amphipathic α-Helix Bundle Organization of Lipid-Free Chicken Apolipoprotein A-I," *Biochemistry* 38(14):4327-4334.

Kiss, R.S. et al. (2001). "Functional Similarities of Human and Chicken Apolipoprotein A-I: Dependence on Secondary and Tertiary Rather than Primary Structure," *Biochimica et Biophysica Acta* 1531:251-259.

Kiss, R.S. et al. (Jun. 13, 2003). "Structure-Guided Protein Engineering Modulates Helix Bundle Exchangeable Apolipoprotein Properties," *The Journal of Biological Chemistry* 278(24):21952-21959.

Kwoh, D.Y. et al. (Feb. 1989). "Transcription-Based Amplification System and Detection of Amplified Human Immunodeficiency Virus Type 1 with a Bead-Based Sandwich Hybridization Format," *Proc. Natl. Acad. Sci. USA* 86:1173-1177.

Lagerstedt, J.O. et al. (Jan. 4, 2007). "EPR Spectroscopy of Site-Directed Spin Labels Reveals the Structural Heterogeneity in the N-Terminal Domain of APO-AI in Solution," *JBC Papers in Press*, located at <http://www.jbc.org/cgi//doi/10.1074/jbc.M608717200>, 12 pages.

Liu, H. et al. (Jan. 1993). "Prevention of Phospholipase-C Induced Aggregation of Low Density Lipoprotein by Amphipathic Apolipoproteins," *FEBS* 316(1):27-33.

Martin, D.D.O. et al. (Jul. 21, 2006). "Apolipoprotein A-I Assumes a "Looped Belt" Conformation on Reconstituted High Density Lipoprotein," *The Journal of Biological Chemistry* 281(29):20418-20426.

Narang, S.A. et al. (1979). "Improved Phosphotriester Method For the Synthesis of Gene Fragments," Chapter 6 in *Methods in Enzymology*, Academic Press, Inc., 68:90-99.

Narayanaswami, V. et al. (1994). "Structural and Binding Characteristics of the Carboxyl Terminal Fragment of Apolipophorin III from *Manduca sexta*," *Biochemistry* 33(45):13312-13320.

Narayanaswami, V. et al. (1995). "Spectroscopic and Lipid Binding Studies on the Amino and Carboxyl Terminal Fragments of *Locusta migratoria* Apolipophorin III," *Biochemistry* 34(37):11822-11830.

Narayanaswami, V. et al. (Oct. 1, 1996). "Fluorescence Studies of Lipid Association-Induced Conformational Adaptations of an Exchangeable Amphipathic Apolipoprotein," *Archives of Biochemistry and Biophysics* 334(1):143-150.

Narayanaswami, V. et al. (Oct. 25, 1996). "Disulfide Bond Engineering to Monitor Conformational Opening of Apolipophorin III During Lipid Binding," *The Journal of Biological Chemistry* 271(43):26855-26862.

Narayanaswami, V. et al. (Apr. 1999). "A Molecular Trigger of Lipid Binding-Induced Opening of a Helix Bundle Exchangeable Apolipoprotein," *Proc. Natl. Acad. Sci. USA* 96:4366-4371.

Narayanaswami, V. et al. (2000). "Spectroscopic Characterization of the Conformational Adaptability of *Bombyx mori* Apolipophorin III," *Eur. J. Biochem.* 267:728-736.

Narayanaswami, V. et al. (Oct. 12, 2001). "Lipid Association-Induced N- and C-Terminal Domain Reorganization in Human Apolipoprotein E3," *The Journal of Biological Chemistry* 276(41):37853-37860.

Narayanaswami, V. et al. (Apr. 2, 2004). "Helix Orientation of the Functional Domains in Apolipoprotein E in Discoidal High Density Lipoprotein Particles," *The Journal of Biological Chemistry* 279(14):14273-14279.

Nelson, K.G. et al. (Apr. 2006). "Nanodisk-Associated Amphotericin B Clears *Leishmania major* Cutaneous Infection in Susceptible BALB/c Mice," *Antimicrobial Agents and Chemotherapy* 50(4):1238-1244.

Nguyen, T-S. et al. (Jul. 23, 2007). "Amphotericin B Induces Interdigitation of Apolipoprotein Stabilized Nanodisk Bilayers," submitted for publication to *Biochimica Biophysica Acta*, 29 pages.

Oda, M.N. et al. (2001). "Cysteine Substitutions in Apolipoprotein A-I Primary Structure Modulate Paraoxonase Activity," *Biochemistry* 40(6):1710-1718.

Oda, M.N. et al. (2002). "Paraoxonase 1 Overexpression in Mice and Its Effect on High-Density Lipoproteins," *Biochemical and Biophysical Research Communication* 290(3):921-927.

Oda, M.N. et al. (e-pub. May 19, 2003). "The C-Terminal Domain of Apolipoprotein A-I Contains a Lipid-Sensitive Conformational Trigger," *Nature Structural Biology*, pp. 1-6.

Oda, M.N. et al. (2006). "Reconstituted High Density Lipoprotein Enriched with the Polyene Antibiotic Amphotericin B," *J. Lipid Res.* 47:260-267.

Raussens, V. et al. (May 26, 1995). "Alignment of the Apolipophorin-III α-Helices in Complex with Dimyristoylphosphatidylcholine," *The Journal of Biological Chemistry* 270(21):12542-12547.

Raussens, V. et al. (Sep. 20, 1996). "Hydrogen/Deuterium Exchange Kinetics of Apolipophorin-III in Lipid-Free and Phospholipid-Bound States," *The Journal of Biological Chemistry* 271(38):23089-23095.

Raussens, V. et al. (Oct. 2, 1998). "The Low Density Lipoprotein Receptor Active Conformation of Apolipoprotein E," *The Journal of Biological Chemistry* 273(40):25825-25830.

Raussens, V. et al. (Dec. 8, 2000). "Structural Characterization of a Low Density Lipoprotein Receptor-Active Apolipoprotein E Peptide, ApoE3-(126-183)," *The Journal of Biological Chemistry* 275(49):38329-38336.

Raussens, V. et al. (Jul. 11, 2003). "Lipid-Bound Structure of an Apolipoprotein E-Derived Peptide," *The Journal of Biological Chemistry* 278(28):25998-26006.

Redmond, K.A. et al. (2007). "All-*trans*-Retinoic Acid Nanodisks," *Int. J. Pharma.* pp. 1-5.

Ryan, R.O. et al. (Jan. 25, 1993). "Conformational, Thermodynamic, and Stability Properties of *Manduca sexta* Apolipophorin III," *The Journal of Biological Chemistry* 268(3):1525-1530.

Ryan, R.O. et al. (2003). "Lipid-Protein Nanodisk Drug Delivery Vehicle," Abstract of Poster Presentation, *US and Japan Symposium on Drug Delivery*, Dec. 14-19, 2003, one page.

Sahoo, D. et al. (Jan. 16, 1998). "Fluorescence Studies of Exchangeable Apolipoprotein-Lipid Interactions," *The Journal of Biological Chemistry* 273(3):1403-1408.

Sahoo, D. et al. (2000). "Pyrene Excimer Fluorescence: A Spatially Sensitive Probe to Monitor Lipid-Induced Helical Rearrangement of Apolipophorin III," *Biochemistry* 39(22):6594-6601.

Sahoo, D. et al. (2002). "Lipid-Triggered Conformational Switch of Apolipophorin III Helix Bundle to an Extended Helix Organization." *J. Mol. Biol.* 321:201-214.

Singh, T.K.A. et al. (1994). "Effect of Phospholipase C and Apolipophorin III on the Structure and Stability of Lipophorin Subspecies," *Journal of Lipid Research* 35:1561-1569.

Smith, J.D. et al. (2004). "ABCA1 Mediates Concurrent Cholesterol and Phospholipid Efflux to ApoAI," *J. Lipid Res.* 45(4), 37 pages.

Tufteland, M. et al. (Jan. 19, 2007). "Peptide Stabilized Amphotericin B Nanodisks," *Peptides* 28:741-746.

Wang, J. et al. (Jul. 18, 1997). "Insight into Lipid Surface Recognition and Reversible Conformational Adaptations of an Exchangeable Apolipoprotein by Multidimensional Heteronuclear NMR Techniques," *The Journal of Biological Chemistry* 272(29):17912-17920.

Wang, J. et al. (1998). "Interhelical Contacts are Required for the Helix Bundle Fold of Apolipophorin III and Its Ability to Interact with Lipoproteins," *Protein Science* 7:336-341.

Wang, J. et al. (1998). "NMR Evidence for a Conformational Adaptation of Apolipophorin III Upon Lipid Association," *Biochem. Cell Biol.* 76:276-283.

Wang, J. et al. (Feb. 5, 2002). "Structural Basis for the Conformational Adaptability of Apolipophorin III, a Helix-Bundle Exchangeable Apolipoprotein," *Proc. Natl. Acad. Sci. USA* 99(3):1188-1193.

Weers, P.M.M. et al. (1994). "Factors Affecting the Stability and Conformation of *Locusta migratoria* Apolipophorin III," *Biochemistry* 33(12):3617-3624.

Weers, P.M.M. et al. (1998). "Recombinant Locust Apolipophorin III: Characterization and NMR Spectroscopy," *Biochimica et Biophysics Acta* 1393:99-107.

Weers, P.M.M. et al. (Jul. 30, 1999). "Interaction of an Exchangeable Apolipoprotein with Phospholipid Vesicles and Lipoprotein Particles," *The Journal of Biological Chemistry* 274(31):21804-21810.

Weers, P.M.M. et al. (2000). "Interaction of Locust Apolipophorin III with Lipoproteins and Phospholipid Vesicles: Effect of Glycosylation," *Journal of Lipid Research* 41:416-423.

Weers, P.M.M. et al. (2000). "Lipid Binding of the Exchangeable Apolipoprotein Apolipophorin III Induces Major Changes in Fluorescence Properties of Tryptophans 115 and 130," *Biochemistry* 39(23):6874-6880.

Weers, P.M.M. et al. (2001). "Conformational Changes of an Exchangeable Apolipoprotein, Apolipophorin III from *Locusta migratoria*, at Low pH: Correlation with Lipid Binding," *Biochemistry* 40(25):7754-7760.

Weers, P.M.M. et al. (2003). "Lipid Binding Ability of Human Apolipoprotein E N-Terminal Domain Isoforms: Correlation with Protein Stability?" *Biophysical Chemistry* 100:481-492.

Wientzek, M. et al. (Feb. 11, 1994). "Binding of Insect Apolipophorin III to Dimyristoylphosphatidylcholine Vesicles," *The Journal of Biological Chemistry* 269(6):4605-4612.

Zhang, Y. et al. (1993). "Calorimetric and Spectroscopic Studies of the Interaction of *Manduca sexta* Apolipophorin III with Zwitterionic, Anionic, and Nonionic Lipids," *Biochemistry* 32(15):3942-3952.

Anonymous. (1996). *Webster's Ninth New Collegiate Dictionary*, Merriam-Webster Inc.:Springfield, MA, definitions of "solicitor general" through "somatostatin," one page.

Bittman, R. et al. (1974). "Interaction of Filipin III and Amphotericin B with Lecithin-Sterol Vesicles and Cellular Membranes. Spectral and Electron Microscope Studies," *Biochemistry* 13(7):1364-1373.

Fujii, G. et al. (1997). "The Formation of Amphotericin B Ion Channels in Lipid Bilayers," *Biochemistry* 36(16):4959-4968.

Gagoś, M. et al. (Sep.-Oct. 2005). "Binding of Antibiotic Amphotericin B to Lipid Membranes: Monomolecular Layer Technique and Linear Dichroism-FTIR Studies," *Molecular Membrane Biology* 22(5):433-442.

Goormaghtigh, E. et al. (1999). "Attenuated Total Reflection Infrared Spectroscopy of Proteins and Lipids in Biological Membranes," *Biochimca et Biophysica Acta* 1422:105-185.

Hargreaves, P.L. et al. (2006). "Spectroscopic Studies of Amphotericin B Solubilized in Nanoscale Bilayer Membranes," *Biochimica et Biophysica Acta* 1758:38-44.

Kader, A. et al. (2002). "Loading Anticancer Drugs into HDL as Well as LDL has Little Affect on Properties of Complexes and Enhances Cytotoxicity to Human Carcinoma Cells," *Journal of Controlled Release* 80:29-44.

Lacko, A.G. et al. (Jul.-Aug. 2002). "High Density Lipoprotein Complexes as Delivery Vehicles for Anticancer Drugs," *Anticancer Research* 22(4):2045-2050.

Tufteland, M. et al. (2008). "Nanodisks Derived from Amphotericin B Lipid Complex," In press, *Journal of Pharmaceutical Sciences*, 24 pages.

Blanche, P. J. et al. (1981). "Characterization of Human-Density Lipoproteins by Gradient Gel Electrophoresis," *Biochim Biophys. Acta.* 665(3):408-419.

Dass, C. R. et al. (2000). "Apolipoprotein A-1, Phospholipid Vesicles, and Cyclodextrins as Potential Anti-Atherosclerotic Drugs: Delivery, Pharmacokinetics, and Efficacy," *Drug Delivery* 7:161-182.

Dass, C. R. et al. (2000). "Apolipoprotein A-I, Cyclodextrins and Liposomes As Potential Drugs for the Reversal of Atherosclerosis. A Review," *J. Pharm. Pharmacol.* 52:731-761.

Dinur, T. et al. (1992). "Toward Gene Therapy for Niemann-Pick Disease (NPD): Separation of Retrovirally Corrected and Noncorrected NPD Fibroblasts Using a Novel Fluorescent Sphingomyelin," *Human Gene Therapy* 3:633-639.

Fisher, C. A. et al. (1997). "Bacterial Overexpression, Isotope Enrichment, and NMR Analysis of the N-Terminal Domain of Human Apolipoprotein E," *Biochem. Cell Biol.* 75(1):45-53.

Goldstein, J. L. et al. (1979). Binding Site on Macrophages that Mediates Uptake and Degradation of Acetylated Low Density Lipoprotein, Producing Massive Cholesterol Deposition *PNAS USA* 76:333-337.

Granich, G. G. et al. (1986). "Sensitive High-Pressure Liquid Chromatographic Assay for Amphotericin B Which Incorporates an Internal Standard," *Antimicrob. Agents Chemother.* 29(4):584-588.

Kagkadis, K. A et al. (1996). "A Freeze-Dried Injectable Form of Ibuprofen: Development and Optimisation Using Response Surface Methodology," *PDA J. Pharm Sci. and Technol.* 50(5):317-323.

Madden, T.D. et al. (1990). "Incorporation of Amphotericin B Into Large Unilamellar Vesicles Composed of a Phosphatidylglycerol," *Chemistry and Physics of Lipids* 52:189-198.

Narayanaswami, V. et al.(2000). "Molecular Basis of Exchangeable Apolipoprotein Function," *Biochimica et Biophysica Acta* 1483:15-36.

Oda, M. N. et al. (2002). "The C-Terminal Domain of Apolipoprotein A-I Contains A Lipid-Sensitive Conformational Trigger," *Nature* 10(6):455-460.

Rajan, V. P. et al. (1988). "Differential Uptake and Metabolism of Free and Esterfied Cholesterol from High-Density Lipoproteins in the Ovary," *Biochimica et Biophysica Acta* 959:206-213.

Ramprasad, M. P. et al. (2002). "Sustained-Delivery of an Apolipoprotein E-Peptidomimeitic Using Multivesicular Liposomes Lowers Serum Cholesterol Levels," *Journal of Controlled Release* 79:207-218.

Rensen, P.C.N. et al. (1997). "Human Recombinant Apolipoprotein E-Enriched Liposomes Can Mimic Low-Density Lipoproteins As Carriers for the Site-Specific Delivery of Antitumor Agents," *Molecular Pharmacology* 52(3):445-455.

Ryan, R.O. et al. (2003). "Optimized Bacterial Expression of Human Apolipoprotein A-I," *Protein Expression and Purification* 27:98-103.

Segrest, J.P. et al. (1994). "The Amphipathic α Helix: A Multifunctional Structural Motif in Plasma Apolipoproteins," *Adv. Protein Chem*. 45:303-369.

Schouten, D. et al. (1993). "Development of Lipoprotein-Like Lipid Particles for Drug Targeting: Neo-High Density Lipoproteins," *Molecular Pharmacology* 44(2):486-492.

Sweetana, S. et al. (1996). "Solubility Principles and Practices for Parenteral Drug Dosage Form Development," *PDA J. Pharm Sci Tech* 50(5):330-342.

Versluis, A. J. et al. (1998). Synthesis of a Lipophilic Daunorubicin Derivative and Its Incorporation Into Lipidic Carriers Developed for LDL Receptor-Mediated Tumor Therapy, *Pharmaceutical Research* 15(4):531-537.

Versluis, A. J. et al. (1998). "Low-Density Lipoprotein Receptor-Mediated Delivery of a Lipoholic Daunorubicin Derivative to B16 Tumours in Mice Using Apolipoprotein E-Enriched Liposomes," *British Journal of Cancer* 78(12):1607-1614.

Versluis, A. J. et al. (1999). "Stable Incorporation of a Lipophilic Daunorubicin Produg Into Apolipoprotein E-Exposing Liposomes Induces Uptake of Prodrug Via Low-Density Lipoprotein Receptor in Vivo," *The Journal of Pharmacology and Experimental Therapeutics* 289(1):1-7.

Von Dardel, O. V. (1976). "Diazepam in Emulsion Form for Intravenous Usage," *Acta Anaesth Scand*. 20:221-224.

Wasan,K.M. et al. (1994). "Influence of Lipoproteins on Renal Cytotoxicity and Antifungal Activity of Amphotericin B," *Antimicrobial Agents and Chemotherapy* 38(2):223-227.

Weers, P.M. et al. (2001). "Modulation of the Lipid Binding Properties of the N-Terminal Domain of Human Apolipoprotein E3," *Eur. J. Biochem*. 268:3728-3735.

Anonymous, (Apr. 30, 2004). "Sushi-Like Discs Give Inside View of Elusive Membrane Proteins," *Science* 304:674.

Anonymous, (Jul. 12, 2004). "Nanodisc: Enabling the Biochemistry of Membrane-Associated Molecules for Drug Discovery and Novel Therapeutic Applications," located at < http://www.nanodiscinc.com/technology.htm> and <http://www.nanodiscinc.com/press.shtml> visited on Jul. 12, 2004, 3 pages.

Barwicz, J. et al., (Oct. 1992). "Effects of the Aggregation State of Amphotericin B on Its Toxicity to Mice," *Antimicrobial Agents and Chemotherapy* 36(10):2310-2315.

Bayburt, T. H. et al., (2000). "Single Molecule Height Measurements on a Membrane Protein in Nanometer-Scale Phospholipid Bilayer Disks," *Langmuir* 16:5993-5997.

Bayburt, T. H. et al., (2002). "Self-Assembly of Discoidal Phospholipid Bilayer Nanoparticles With Membrane Scaffold Proteins," *Nano Letters* 2(8):853-856.

Bayburt, T. H. et al., (Nov. 2003). "Self-Assembly of Single Integral Membrane Proteins Into Soluble Nanoscale Phospholipid Bilayers," *Protein Sci*. 12:2476-2481.

Burke, T. G. et al. (May 25, 1993). "Lipid Bilayer Partitioning and Stability of Camptotech in Drugs," *Biochemistry* 32(20):5352-5364.

Carlson, J. W. et al., (2000). "Nanopatterning Phospholipid Bilayers," *Langmuir* 16:3927-3931.

Clemons, K. V. et al., (Apr. 1998). "Comparison of Fungizone, Amphotec, AmBisome, and Abelcet for Treatment of Systemic Murine Cryptococcosis," *Antimicrobial Agents and Chemotherapy* 42(4):899-902.

Denisov, I. G. et al., (2004). "Directed Self-Assembly of Monodisperse Phospholipid Bilayer Nanodiscs With Controlled Size," *J. Am. Chem. Soc*. 126:3477-3487.

International Search Report mailed on Aug. 6, 2004, for PCT patent application No. PCT/US2004/004295 filed Feb. 13, 2004, 7 pages.

Lister, J. (1996). "Amphotericin B Lipid Complex (Abelcet) in the Treatment of Invasive Mycoses; the American Experience," *European Journal of Haematology Supplementum* 57:18-23.

Lundberg, B. B. (1998). "Biologically Active Camptothecin Derivatives for Incorporation Into Liposome Bilayers and Lipid Emulsions," *Anti-Cancer Drug Design Basingstoke* 13(5):453-461.

Van Etten, E. W. M. et al., (Sep. 1998). "Superior Efficacy of Liposomal Amphotericin B With Prolonged Circulation in Blood in the Treatment of Severe Candidiasis in Leukopenic Mice," *Antimicrobial Agents and Chemotherapy* 42(9):2431-2433.

Bayburt, T.H. et al. (1998). "Reconstitution and Imaging of a Membrane Protein in a Nanometer-Size Phospholipid Bilayer," *J. Struct. Biol*. 123:37-44.

Nichols, A.V. et al. (1983). "Characterization of Discoidal Complexes of Phosphatidylcholine, Apolipoprotein A-I and Cholesterol by Gradient Gel Electrophoresis," *Biochim. Biophys. Acta* 750:353-364.

Nichols, A.V. et al. (1987). "Pathways in the Formation of Human Plasma High Density Lipoprotein Subpopulations Containing Apolipoprotein A-1 Without Apolipoprotein A-II," *J. Lipid Res*. 28:719-732.

Sparks, D.L. et al. (Dec. 25, 1992). "The Conformation of Apolipoprotein A-I in Discoidal and Spherical Recombinant High Density Lipoprotein Particles," *J. Biol. Chem*. 267(36):25830-25838.

Boadu, E. et al. (2008). "Cellular Cholesterol Substrate Pools for Adenosine-triphosphate Cassette Transporter A1 -dependent High Density Lipoprotein Formation," *Curr. Opin. Lipidol*. 19:270-276.

* cited by examiner

Targeting: α-Mating Factor

Synergistic Effector: Histatin-5

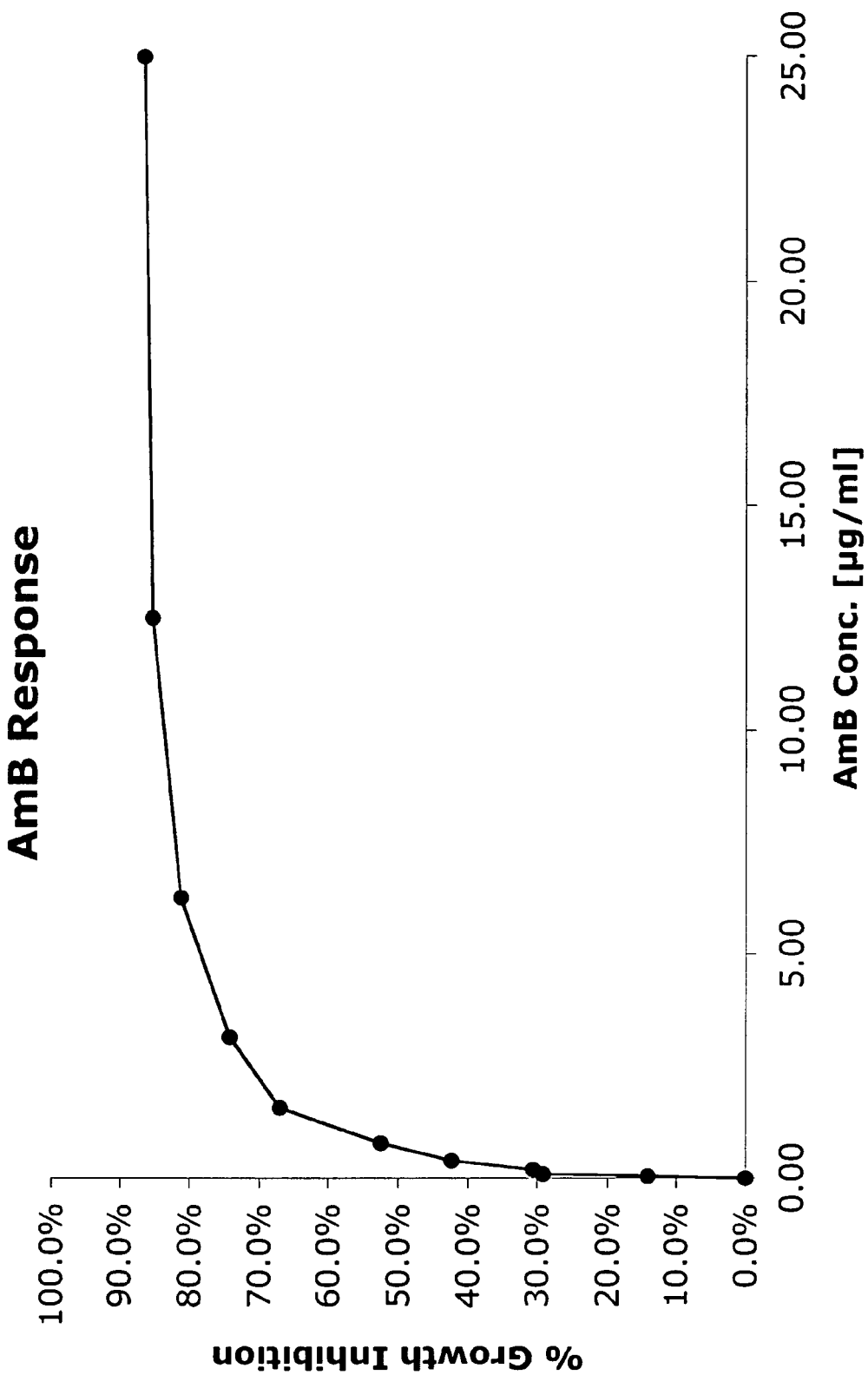

LIPOPHILIC DRUG DELIVERY VEHICLE AND METHODS OF USE THEREOF

CROSS-REFERENCE TO RELATED APPLICATIONS

This application claims the benefit of U.S. Provisional Patent Application Ser. No. 60/447,508, filed Feb. 14, 2003, and No. 60/508,035, filed Oct. 1, 2003, the disclosures of both of which are incorporated herein by reference in their entireties.

STATEMENT REGARDING FEDERALLY SPONSORED RESEARCH OR DEVELOPMENT

This invention was made in part during work supported by grant no. HL064159 from the National Institutes of Health. The government has certain rights in the invention.

FIELD OF THE INVENTION

This application relates to compositions and methods for delivery of bioactive agents. In particular, the application relates to bioactive agent delivery particles that include a lipid binding polypeptide, a lipid bilayer, and a bioactive agent.

BACKGROUND OF THE INVENTION

Bioactive substances such as therapeutic agents, vaccine immunogens, and nutrients often cannot be administered in pure form, but must be incorporated into biocompatible formulations that enhance solubility of the bioactive material and package it in a suitable form to achieve optimal beneficial effects while minimizing undesirable side effects. Efficient delivery of bioactive agents is often hindered by a short clearance time of an agent in the body, inefficient targeting to a site of action, or the nature of the bioactive agent itself, for example, poor solubility in aqueous media or hydrophobicity. Thus, many formulation strategies have been developed to improve delivery, including controlled release formulations, emulsions, and liposomal preparations.

Liposomal pharmaceutical delivery systems have been described. Liposomes are completely closed, spherical lipid bilayer membranes containing an entrapped aqueous volume. The lipid bilayer includes two lipid monolayers composed of lipids having a hydrophobic tail region and a hydrophilic head region. The structure of the membrane bilayer is such that the hydrophobic, nonpolar tails of the lipid molecules orient toward the center of the bilayer while the hydrophilic heads orient toward the aqueous phases both on the exterior and the interior of the liposome. The aqueous, hydrophilic core region of a liposome may include a dissolved bioactive substance.

Delivery of pharmaceutically useful hydrophobic substances is often particularly problematic because they are insoluble or poorly soluble in an aqueous environment. For hydrophobic compounds used as pharmaceuticals, direct injection may be impossible or highly problematic, resulting in such dangerous conditions as hemolysis, phlebitis, hypersensitivity, organ failure, and/or death. There is a need for improved formulations for hydrophobic bioactive substances that will promote stability in an aqueous environment and allow efficient delivery of such substances to a desired site of action.

BRIEF SUMMARY OF THE INVENTION

The invention provides compositions and methods for delivery of a bioactive agent to an individual.

In one aspect, the invention provides a bioactive agent delivery particle that includes a lipid binding polypeptide, a lipid bilayer with an interior that includes a hydrophobic region, and a bioactive agent associated with the hydrophobic region of the lipid bilayer. Bioactive agent delivery particles generally do not include a hydrophilic or aqueous core.

Bioactive agent delivery particles include one or more bioactive agents that include at least one hydrophobic region and are incorporated into, or associated with, the hydrophobic interior of the lipid bilayer. The hydrophobic region(s) of a bioactive agent are generally associated with hydrophobic surfaces in the interior of the lipid bilayer, e.g., fatty acyl chains. In one embodiment, the bioactive agent is amphotericin B (AmB). In another embodiment, the bioactive agent is camptothecin.

Particles are typically disc shaped, with a diameter in the range of about 7 to about 29 nm.

Bioactive agent delivery particles include bilayer-forming lipids, for example phospholipids. In some embodiments, a bioactive agent delivery particle includes both bilayer-forming and non-bilayer-forming lipids. In some embodiments, the lipid bilayer of a bioactive agent delivery particle includes phospholipids. In one embodiment, the phospholipids incorporated into a delivery particle include dimyristoylphosphatidylcholine (DMPC) and dimyristoylphosphatidylglycerol (DMPG). In one embodiment, the lipid bilayer includes DMPC and DMPG in a 7:3 molar ratio.

In a preferred embodiment, the lipid binding polypeptide is an apolipoprotein. The predominant interaction between lipid binding polypeptides, e.g., apolipoprotein molecules, and the lipid bilayer is generally a hydrophobic interaction between residues on a hydrophobic face of an amphipathic structure, e.g., an $\alpha$-helix of the lipid binding polypeptide and fatty acyl chains of lipids on an exterior surface at the perimeter of the particle. Particles of the invention may include exchangeable and/or non-exchangeable apolipoproteins. In one embodiment, the lipid binding polypeptide is Apolipoprotein A-I (ApoA-I).

In some embodiments, particles are provided that include lipid binding polypeptide molecules, e.g., apolipoprotein molecules, that have been modified to increase stability of the particle. In one embodiment, the modification includes introduction of cysteine residues to form intramolecular and/or intermolecular disulfide bonds.

In another embodiment, particles are provided that include a chimeric lipid binding polypeptide molecule, e.g., a chimeric apolipoprotein molecule, with one or more bound functional moieties, for example one or more targeting moieties and/or one or more moieties having a desired biological activity, e.g., antimicrobial activity, which may augment or work in synergy with the activity of a bioactive agent incorporated into the delivery particle.

In another aspect, a pharmaceutical composition is provided that includes a bioactive agent delivery particle in a pharmaceutically acceptable carrier. A method for administering a bioactive agent to an individual is also provided, which includes administering a pharmaceutical composition containing bioactive agent delivery particles in a pharmaceutically acceptable carrier to the individual. In some embodiments, a therapeutically effective amount of the bioactive agent is administered in a pharmaceutically acceptable carrier. In some embodiments, administration is parenteral, for example intravenous, intramuscular, transmucosal, or intrathecal. In other embodiments, particles are administered as an aerosol. In some embodiments, the bioactive agent is formulated for controlled release. In one embodiment, a method is provided for treating a fungal infection in an individual, including administering a anti-fungal agent, for example, AmB, incorporated into bioactive agent delivery particles of the invention, often in a therapeutically effective amount in a pharmaceutically acceptable carrier. In another embodiment, a method is provided for treating a tumor in an individual, including administering an anti-tumor agent, for example, camptothecin, incorporated into bioactive agent delivery particles of the invention, often in a therapeutically effective amount in a pharmaceutically acceptable carrier. In one embodiment, the bioactive agent delivery particles include a lipid binding polypeptide with an attached vasoactive intestinal peptide targeting moiety, and the tumor is a breast tumor.

In a still further aspect, processes are provided for formulating bioactive agent delivery particles as described above. In one embodiment, the formulation process includes contacting a mixture that includes bilayer-forming lipids and a bioactive agent to form a lipid vesicle-bioactive agent mixture, and contacting the lipid vesicle-bioactive agent mixture with a lipid binding polypeptide. In another embodiment, the formulation process includes formation of a dispersion of pre-formed bilayer-containing lipid vesicles to which a bioactive agent, dissolved in an appropriate solvent, is added. Appropriate solvents for solubilizing a bioactive agent for this procedure include solvents with polar or hydrophilic character that are capable of solubilizing a bioactive agent to be incorporated into a delivery particle of the invention. Examples of suitable solvents include, but are not limited to, dimethylsulfoxide (DMSO) and dimethylformamide. To the vesicle/bioactive agent mixture, lipid binding polypeptides are added, followed by incubation, sonication, or both. In one embodiment, the bioactive agent incorporated into a delivery particle by any of the above processes is amphotericin B. In one embodiment, the amphotericin B is solubilized in DMSO. In another embodiment, the bioactive agent is camptothecin. In one embodiment, the camptothecin is solubilized in DMSO.

The invention includes bioactive agent delivery particles prepared according to any of the processes described above, and pharmaceutical compositions including particles prepared according to any of the above processes and a pharmaceutically acceptable carrier.

In another aspect, the invention provides kits including any of the bioactive agent delivery particles or pharmaceutical compositions described above, or delivery particles prepared by any of the above methods, and/or reagents for formulating the particles and/or instructions for use in a method for administering a bioactive agent to an individual.

BRIEF DESCRIPTION OF THE DRAWINGS

FIG. 8 graphically depicts antifungal activity of AmB-containing bioactive agent delivery particles against *Saccharomyces cerevisiae* (*S. cerevisiae*) in culture, as described in Example 2.

DETAILED DESCRIPTION OF THE INVENTION

The invention provides compositions and methods for delivery of a bioactive agent to an individual. Delivery vehicles are provided in the form of a bioactive agent incorporated into a particle that includes a lipid binding polypeptide and a lipid bilayer. The interior of the particle includes a hydrophobic region of the lipid bilayer that includes hydrophobic portions of lipid molecules, e.g., fatty acyl chains of lipids, in contrast to liposomes, which include a wholly enclosed aqueous interior surrounded by lipid hydrophilic surfaces of a bilayer. The hydrophobic nature of the interior of a particle of the invention permits incorporation of hydrophobic molecules, for example, by intercalation between lipid molecules in the bilayer or sequestration into the hydrophobic region between leaflets of the bilayer. A bioactive agent that includes at least one hydrophobic region may be incorporated into the hydrophobic interior of the particle. As used herein, "incorporation" of a bioactive agent into the hydrophobic region of a lipid bilayer refers to solubilization into or association with a hydrophobic region or hydrophobic portions of lipid molecules of the bilayer, e.g., fatty acyl chains of lipids that form the bilayer, or intercalation with the fatty acyl chains.

The particles are generally disc shaped, with a diameter in the range of about 7 to 29 nm, as determined by native pore limiting gradient gel electrophoresis, in comparison with standards of known Stokes' diameter, as described, for example, in Blanche et al. (1981) *Biochim. Biophys. Acta.* 665(3):408-19. In some embodiments, the particles are stable in solution and may be lyophilized for long term storage, followed by reconstitution in aqueous solution. The lipid binding polypeptide component defines the boundary of the discoidal bilayer and provides structure and stability to the particles.

Chimeric lipid binding polypeptide molecules (e.g., apolipoprotein molecules) are also provided and may be used to incorporate various additional functional properties into the delivery particles of the invention.

The particles may be administered to an individual to deliver a bioactive agent to the individual.

Bioactive Agent Delivery Particles

The invention provides a "particle" (also termed "delivery particle" or "bioactive agent delivery particle" herein) that includes one or more types of lipid binding polypeptide, a lipid bilayer comprising one or more types of bilayer-forming lipid, and one or more bioactive agents. In some embodiments, a delivery particle also includes one or more types of non-bilayer-forming lipid. Compositions including the particles are also provided. In one embodiment, a pharmaceutical composition is provided that includes delivery particles and a pharmaceutically acceptable carrier.

Figure 6A:
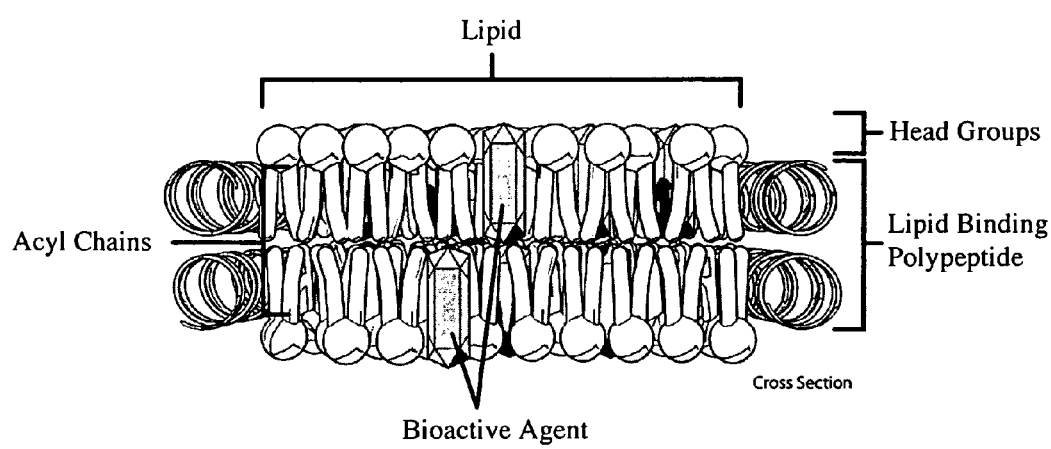
FIG. 6 schematically illustrates the shape and molecular organization of a bioactive agent delivery particle.
Figure 6B:
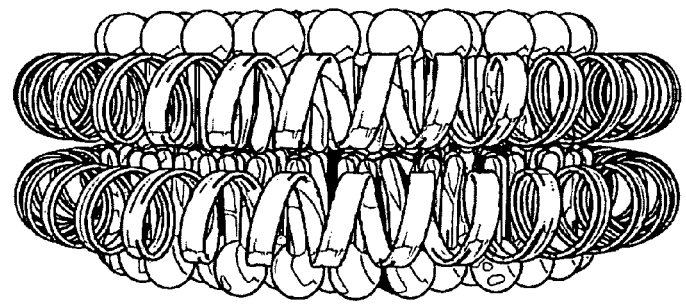

The interior of a particle includes a hydrophobic region (e.g., comprised of lipid fatty acyl chains). Particles of the invention typically do not comprise a hydrophilic or aqueous core. The particles are generally disc shaped, having a flat, discoidal, roughly circular lipid bilayer circumscribed by amphipathic α-helices and/or β-sheets of the lipid binding polypeptides, which are associated with hydrophobic surfaces of the bilayer around the periphery of the disc. An illustrative example of a disc shaped bioactive agent delivery particle of the invention is schematically depicted in FIG. 6.

Typically, the diameter of a disc shaped delivery particle is about 7 to about 29 nm, often about 10 to about 25 nm, often about 15 to about 20 nm. "Diameter" refers to the diameter of one of the roughly circular shaped faces of the disc.

Lipid Binding Polypeptides

As used herein, a "lipid binding polypeptide" refers to any synthetic or naturally occurring peptide or protein that forms a stable interaction with lipid surfaces and can function to stabilize the lipid bilayer of a particle of the invention. Particles may include one or more types of lipid binding polypeptides, i.e., the lipid binding polypeptides in a single particle may be identical or may be composed of two or more different polypeptide sequences. The lipid binding polypeptides circumscribe the periphery of the particle.

In some embodiments, lipid binding polypeptides useful for producing delivery particles in accordance with the invention include proteins having an amino acid sequence of a naturally occurring protein, or a fragment, natural variant, isoform, analog, or chimeric form thereof, proteins having a non-naturally occurring sequence, and proteins or peptides of any length that possess lipid binding properties consistent with known apolipoproteins, and may be purified from natural sources, produced recombinantly, or produced synthetically. An analog of a naturally-occurring protein may be used. A lipid binding polypeptide may include one or more non-natural amino acids (e.g., D-amino acids), amino acid analogs, or a peptidomimetic structure, in which the peptide bond is replaced by a structure more resistant to metabolic degradation, or individual amino acids are replaced by analogous structures.

In a preferred embodiment, the lipid binding polypeptide is an apolipoprotein. Any apolipoprotein or fragment or analog thereof may be used that is capable of associating with a lipid bilayer to form a disc shaped particle. Particles may include exchangeable, non-exchangeable, or a mixture of exchangeable and non-exchangeable apolipoprotein molecules.

Apolipoproteins generally possess a class A amphipathic α-helix structural motif (Segrest et al. (1994) *Adv. Protein Chem.* 45:303-369), and/or a β-sheet motif. Apolipoproteins generally include a high content of α-helix secondary structure with the ability to bind to hydrophobic surfaces. A characteristic feature of these proteins is their ability to interact with certain lipid bilayer vesicles and to transform them into disc-shaped complexes (for a review, see Narayanaswami and Ryan (2000) *Biochimica et Biophysica Acta* 1483:15-36). Upon contact with lipids, the protein undergoes a conformational change, adapting its structure to accommodate lipid interaction.

Generally, the predominant interaction between apolipoproteins and the lipid bilayer in a particle is through a hydrophobic interaction between residues on the hydrophobic faces of amphipathic α-helices of apolipoprotein molecules and hydrophobic surfaces of lipids, for example, phospholipid fatty acyl chains, at the edge of the bilayer at the periphery of the bioactive agent delivery particle. An amphipathic α-helix of an apolipoprotein molecule includes both a hydrophobic surface in contact with a hydrophobic surface of the lipid bilayer at the periphery of the particle, and a hydrophilic surface facing the exterior of the particle and in contact with the aqueous environment when the particle is suspended in aqueous medium. In some embodiments, an apolipoprotein may include an amphipathic β-sheet structure wherein hydrophobic residues of the β-sheet interact with lipid hydrophobic surfaces at the periphery of the disc.

A bioactive agent delivery particle often comprises about 1 to about 10 molecules of one or more types of apolipoprotein per particle. The amount of amphipathic α-helix contributed by the apolipoproteins in a particle is generally sufficient to cover the otherwise exposed hydrophobic surface of the lipid molecules located at the edge of the disc shaped lipid bilayer (i.e., the periphery of the particle). In one embodiment in which the apolipoprotein is human apolipoprotein A-I (ApoA-I) and the lipid bilayer includes palmitoyloleoylphosphatidylcholine, a particle comprises 2 ApoA-I molecules in a ratio of about 80 molecules of phospholipid to about 1 molecule of ApoA-I.

Figure 7A:
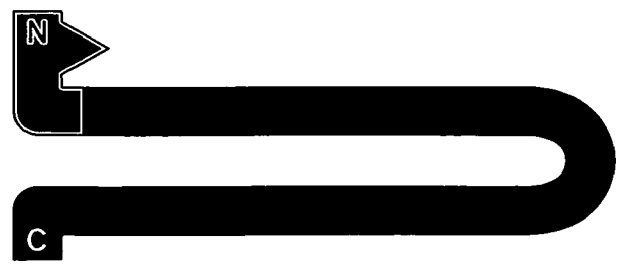
FIG. 7 schematically illustrates chimeric lipid binding polypeptides and their incorporation into a bioactive agent delivery particle. The chimeric proteins may include a targeting moiety (FIG. 7A) or a moiety with a desired biological activity (FIG. 7B).
FIG. 7C schematically illustrates incorporation of the chimeric polypeptides shown in FIGS. 7A and 7B into a bioactive agent delivery particle.
Figure 7B:
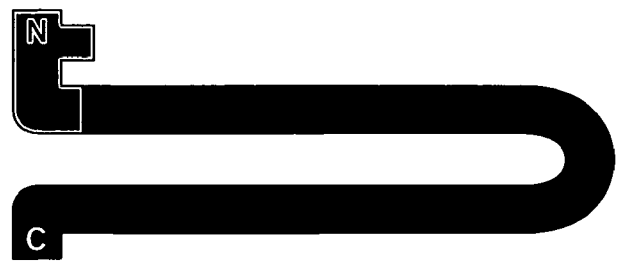
Figure 7C:
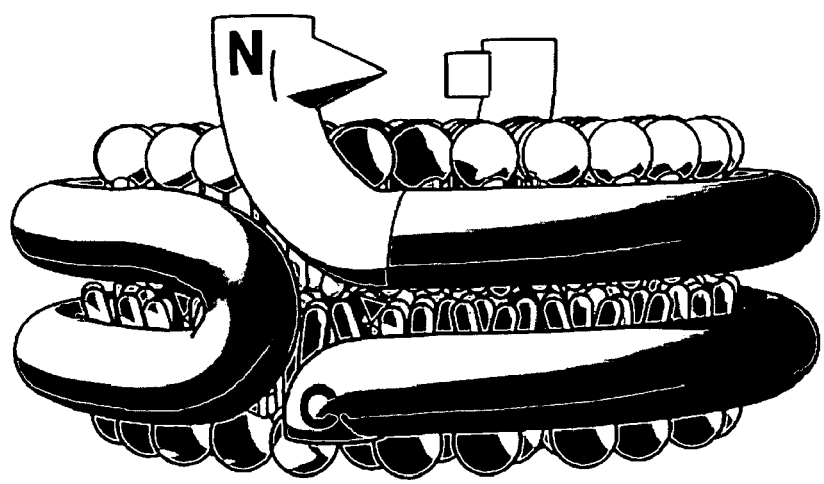

Examples of apolipoproteins which may be used for formation of the delivery particles of the invention include, but are not limited to, ApoA-I, apolipoprotein E (ApoE), and apolipophorin III (ApoIII), apolipoprotein A-IV (ApoA-IV), apolipoprotein A-V (ApoA-V), apolipoprotein C-I (ApoC-I), apolipoprotein C-II (ApoC-II), apolipoprotein C-III (ApoC-III), apolipoprotein D (ApoD), apolipoprotein A-II (ApoA-II), apolipoprotein B-100 (ApoB-100), apolipoprotein J (ApoJ), apolipoprotein H (ApoH), or fragments, natural variants, isoforms, analogs, or chimeric forms thereof. In some embodiments, the apolipoprotein is human ApoA-I. In other embodiments, the apolipoprotein is the C-terminal or N-terminal domain of apolipoprotein E3, or isoforms thereof. In some embodiments, the apolipoprotein includes a functional moiety that has been attached either synthetically or recombinantly, such as a targeting moiety or a moiety having biological activity, that is not intrinsic to the apolipoprotein (see, e.g., FIG. 7).

In some embodiments, an exchangeable apolipoprotein is used. An "exchangeable apolipoprotein" may be displaced from a preformed discoidal particle of the invention by another protein or peptide with lipid binding affinity, without destroying the integrity of the particle. Exchangeable apolipoproteins include synthetic or natural peptides or proteins capable of forming a stable binding interaction with lipids. More than a dozen unique exchangeable apolipoproteins have been identified in both vertebrates and invertebrates (see, e.g., Narayanaswami and Ryan, supra).

In some embodiments, a non-exchangeable apolipoprotein is used. As used herein, "non-exchangeable apolipoprotein" refers to a protein or peptide that forms a stable interaction with lipid surfaces and can function to stabilize the phospholipid bilayer of particles of the invention, but cannot be removed from the surface of the particle without destroying the intrinsic structure of the particle.

Bioactive Agents

The delivery particles include one or more bioactive agents. As used herein, "bioactive agent" refers to any compound or composition having biological, including therapeutic or diagnostic, activity. A bioactive agent may be a pharmaceutical agent, drug, compound, or composition that is useful in medical treatment, diagnosis, or prophylaxis.

Bioactive agents incorporated into delivery particles as described herein generally include at least one hydrophobic (e.g., lipophilic) region capable of associating with or integrating into the hydrophobic portion of a lipid bilayer. In some embodiments, at least a portion of the bioactive agent is intercalated between lipid molecules in the interior of the delivery particle. Examples of bioactive agents that may be incorporated into delivery particles in accordance with the invention include, but are not limited to, antibiotic or antimicrobial (e.g., antibacterial, antifungal, and antiviral) agents, antimetabolic agents, antineoplastic agents, steroids, peptides, proteins, such as, for example, cell receptor proteins, enzymes, hormones, and neurotransmitters, radiolabels such as radioisotopes and radioisotope-labeled compounds, fluorescent compounds, anesthetics, bioactive lipids, anticancer agents, anti-inflammatory agents, nutrients, antigens, pesticides, insecticides, herbicides, or a photosensitizing agent used in photodynamic therapy. In one embodiment, the bioactive agent is the anti-fungal agent AmB. In other embodiments, the bioactive agent is camptothecin, all-trans retinoic acid, annamycin, nystatin, paclitaxel, docetaxel, or etiopurpurins. Bioactive agents that include at least one hydrophobic region are known in the art and include, but are not limited to, ibuprofen, diazepam, griseofulvin, cyclosporin, cortisone, proleukin, etoposide, taxane, α-tocopherol, Vitamin E, Vitamin A, and lipopolysaccharides. See, for example, Kagkadis et al. (1996) *PDA J Pharm Sci Tech* 50(5):317-323; Dardel (1976) *Anaesth Scand* 20:221-24; Sweetana and Akers (1996) *PDA J Pharm Sci Tech* 50(5):330-342; U.S. Pat. No. 6,458,373.

In some embodiments, a bioactive agent incorporated into a delivery particle of the invention is a non-polypeptide. In some embodiments, for administration to an individual, a bioactive agent and the delivery particle that includes the bioactive agent are substantially nonimmunogenic when administered to an individual.

Lipid Bilayer

Particles of the invention include a lipid bilayer, with the generally circular faces of the disc comprising polar head groups facing away from the interior of the particle, and the interior of the particle (i.e., the space between the circular faces) comprising a hydrophobic region of the lipid bilayer that contains hydrophobic portions of bilayer-forming lipid(s) and other lipid components, if present. Hydrophobic surfaces of the lipid molecules at the edge of the bilayer (the surface at the periphery of the bioactive agent delivery particle) contact the lipid binding polypeptides of the particles, as discussed above. Particles may include one or more types of bilayer-forming lipids, or a mixture of one or more types of bilayer-forming and one or more types of non-bilayer-forming lipids. As used herein, "lipid" refers to a substance of biological or synthetic origin that is soluble or partially soluble in organic solvents or which partitions into a hydrophobic environment when present in aqueous phase.

Any bilayer-forming lipid that is capable of associating with a lipid binding polypeptide to form a disc shaped structure may be used in accordance with the invention. As used herein, "bilayer-forming lipid" refers to a lipid that is capable of forming a lipid bilayer with a hydrophobic interior and a hydrophilic exterior. Bilayer-forming lipids include, but are not limited to, phospholipids, sphingolipids, glycolipids, alkylphospholipids, ether lipids, and plasmalogens. One type of bilayer-forming lipid may be used or a mixture of two or more types. In some embodiments, the lipid bilayer includes phospholipids. Examples of suitable phospholipids include, but are not limited to, DMPC, DMPG, POPC, dipalmitoylphosphatidylcholine (DPPC), dipalmitoylphosphatidylserine (DPPS), cardiolipin, dipalmitoylphosphatidylglycerol (DPPG), distearoylphosphatidylglycerol (DSPG), egg yolk phosphatidylcholine (egg PC), soy bean phosphatidylcholine, phosphatidylinositol, phosphatidic acid, sphingomyelin, and cationic phospholipids. Examples of other suitable bilayer-forming lipids include cationic lipids and glycolipids. In one embodiment, the particles include a phospholipid bilayer of DMPC and DMPG, often in a molar ratio of about 7:3. In another embodiment, the particles include a phospholipid bilayer of POPC. In some embodiments, mixtures of bilayer-forming lipids may be used in molar ratios of any of at least about 1:100, 1:50, 1:20, 1:10, 1:5, 3:7, 1:2, or 1:1.

Particles may also include lipids that are not bilayer-forming lipids. Such lipids include, but are not limited to, cholesterol, cardiolipin, phosphatidylethanolamine (this lipid may form bilayers under certain circumstances), oxysterols, plant sterols, ergosterol, sitosterol, cationic lipids, cerebrosides, sphingosine, ceramide, diacylglycerol, monoacylglycerol, triacylglycerol, gangliosides, ether lipids, alkylphospholipids, plasmalogens, prostaglandins, and lysophospholipids. In some embodiments, a lipid used for preparation of a delivery particle may include one or more bound functional moieties, such as targeting moieties, bioactive agents, or tags for purification or detection.

Chimeric Lipid Binding Polypeptides

The invention provides chimeric lipid binding polypeptides, which may be used to prepare the delivery particles described above. A chimeric lipid binding polypeptide may include one or more attached "functional moieties," such as for example, one or more targeting moieties, a moiety having a desired biological activity, an affinity tag to assist with purification, and/or a reporter molecule for characterization or localization studies. An attached moiety with biological activity may have an activity that is capable of augmenting and/or synergizing with the biological activity of a bioactive agent incorporated into the delivery particle. For example, a moiety with biological activity may have antimicrobial (for example, antifungal, antibacterial, anti-protozoal, bacteriostatic, fungistatic, or antiviral) activity. In one embodiment, an attached functional moiety of a chimeric lipid binding polypeptide is not in contact with hydrophobic surfaces of the lipid bilayer when the lipid binding polypeptide is incorporated into a bioactive agent delivery particle. In another embodiment, an attached functional moiety is in contact with hydrophobic surfaces of the lipid bilayer when the lipid binding polypeptide is incorporated into a bioactive agent delivery particle. In some embodiments, a functional moiety of a chimeric lipid binding polypeptide may be intrinsic to a natural protein. In some embodiments, a chimeric lipid binding polypeptide includes a ligand or sequence recognized by or capable of interaction with a cell surface receptor or other cell surface moiety.

In some embodiments, a chimeric lipid binding polypeptide is a chimeric apolipoprotein. In one embodiment, a chimeric apolipoprotein includes a targeting moiety that is not intrinsic to the native apolipoprotein, such as for example, *S. cerevisiae* α-mating factor peptide, folic acid, transferrin, or lactoferrin. In another embodiment, a chimeric apolipoprotein includes a moiety with a desired biological activity that augments and/or synergizes with the activity of a bioactive agent incorporated into the delivery particle, such as for example, histatin-5, magainin peptide, mellitin, defensin, colicin, N-terminal lactoferrin peptide, echinocandin, hepcidin, bactenicin, or cyclosporine. In one embodiment, a chimeric lipid binding polypeptide may include a functional moiety intrinsic to an apolipoprotein. One example of an apolipoprotein intrinsic functional moiety is the intrinsic targeting moiety formed approximately by amino acids 130-150 of human ApoE, which comprises the receptor binding region recognized by members of the low density lipoprotein receptor family. Other examples of apolipoprotein intrinsic functional moieties include the region of ApoB-100 that interacts with the low density lipoprotein receptor and the region of ApoA-I that interacts with scavenger receptor type B 1. In other embodiments, a functional moiety may be added synthetically or recombinantly to produce a chimeric lipid binding polypeptide.

As used herein, "chimeric" refers to two or more molecules that are capable of existing separately and are joined together to form a single molecule having the desired functionality of all of its constituent molecules. The constituent molecules of a chimeric molecule may be joined synthetically by chemical conjugation or, where the constituent molecules are all polypeptides or analogs thereof, polynucleotides encoding the polypeptides may be fused together recombinantly such that a single continuous polypeptide is expressed. Such a chimeric molecule is termed a fusion protein. A "fusion protein" is a chimeric molecule in which the constituent molecules are all polypeptides and are attached (fused) to each other such that the chimeric molecule forms a continuous single chain. The various constituents can be directly attached to each other or can be coupled through one or more linkers.

A "linker" or "spacer" as used herein in reference to a chimeric molecule refers to any molecule that links or joins the constituent molecules of the chimeric molecule. A number of linker molecules are commercially available, for example from Pierce Chemical Company, Rockford Ill. Suitable linkers are well known to those of skill in the art and include, but are not limited to, straight or branched-chain carbon linkers, heterocyclic carbon linkers, or peptide linkers. Where the chimeric molecule is a fusion protein, the linker may be a peptide that joins the proteins comprising a fusion protein. Although a spacer generally has no specific biological activity other than to join the proteins or to preserve some minimum distance or other spatial relationship between them, the constituent amino acids of a peptide spacer may be selected to influence some property of the molecule such as the folding, net charge, or hydrophobicity.

In some embodiments, a chimeric lipid binding polypeptide, such as a chimeric apolipoprotein, is prepared by chemically conjugating the lipid binding polypeptide molecule and the functional moiety to be attached. Means of chemically conjugating molecules are well known to those of skill in the art. Such means will vary according to the structure of the moiety to be attached, but will be readily ascertainable to those of skill in the art.

Polypeptides typically contain a variety of functional groups, e.g., carboxylic acid (—COOH), free amino (—NH2), or sulfhydryl (—SH) groups, that are available for reaction with a suitable functional group on the functional moiety or on a linker to bind the moiety thereto. A functional moiety may be attached at the N-terminus, the C-terminus, or to a functional group on an interior residue (i.e., a residue at a position intermediate between the N- and C-termini) of an apolipoprotein molecule. Alternatively, the apolipoprotein and/or the moiety to be tagged can be derivatized to expose or attach additional reactive functional groups.

In some embodiments, lipid binding polypeptide fusion proteins that include a polypeptide functional moiety are synthesized using recombinant expression systems. Typically, this involves creating a nucleic acid (e.g., DNA) sequence that encodes the lipid binding polypeptide and the functional moiety such that the two polypeptides will be in frame when expressed, placing the DNA under the control of a promoter, expressing the protein in a host cell, and isolating the expressed protein.

Lipid binding polypeptide sequences and sequences encoding functional moieties as described herein may be cloned, or amplified by in vitro methods, such as, for example, the polymerase chain reaction (PCR), the ligase chain reaction (LCR), the transcription-based amplification system (TAS), or the self-sustained sequence replication system (SSR). A wide variety of cloning and in vitro amplification methodologies are well known to persons of skill. Examples of techniques sufficient to direct persons of skill through in vitro amplification methods are found for example, in Mullis et al., (1987) U.S. Pat. No. 4,683,202; *PCR Protocols A Guide to Methods and Applications* (Innis et al. eds) Academic Press Inc. San Diego, Calif. (1990) (Innis); Amheim & Levinson (Oct. 1, 1990) *C&EN* 36-47; *The Journal Of NIH Research* (1991) 3: 81-94; (Kwoh et al. (1989) *Proc. Natl. Acad. Sci. USA* 86: 1173; Guatelli et al. (1990) *Proc. Natl. Acad. Sci. USA* 87, 1874; Lomell et al. (1989) *J. Clin. Chem.*, 35: 1826; Landegren et al., (1988) *Science*, 241: 1077-1080; Van Brunt (1990) *Biotechnology*, 8: 291-294; Wu and Wallace, (1989) *Gene*, 4: 560; and Barringer et al. (1990) *Gene*, 89: 117.

In addition, DNA encoding desired fusion protein sequences may be prepared synthetically using methods that are well known to those of skill in the art, including, for example, direct chemical synthesis by methods such as the phosphotriester method of Narang et al. (1979) *Meth. Enzymol.* 68: 90-99, the phosphodiester method of Brown et al. (1979) *Meth. Enzymol.* 68: 109-151, the diethylphosphoramidite method of Beaucage et al. (1981) *Tetra. Lett.*, 22: 1859-1862, or the solid support method of U.S. Pat. No. 4,458,066.

A nucleic acid encoding a chimeric lipid binding polypeptide fusion polypeptide can be incorporated into a recombinant expression vector in a form suitable for expression in a host cell. As used herein, an "expression vector" is a nucleic acid which, when introduced into an appropriate host cell, can be transcribed and translated into a polypeptide. The vector may also include regulatory sequences such as promoters, enhancers, or other expression control elements (e.g., polyadenylation signals). Such regulatory sequences are known to those skilled in the art (see, e.g., Goeddel (1990) *Gene Expression Technology: Meth. Enzymol.* 185, Academic Press, San Diego, Calif.; Berger and Kimmel, *Guide to Molecular Cloning Techniques, Methods in Enzymology* 152 Academic Press, Inc., San Diego, Calif.; Sambrook et al. (1989) *Molecular Cloning—A Laboratory Manual* (2nd ed.) Vol. 1-3, Cold Spring Harbor Laboratory, Cold Spring Harbor Press, NY, etc.).

In some embodiments, a recombinant expression vector for production of a chimeric lipid binding polypeptide is a plasmid or cosmid. In other embodiments, the expression vector is a virus, or portion thereof, that allows for expression of a protein encoded by the nucleic acid introduced into the viral nucleic acid. For example, replication defective retroviruses, adenoviruses and adeno-associated viruses can be used. Expression vectors may be derived from bacteriophage, including all DNA and RNA phage (e.g., cosmids), or viral vectors derived from all eukaryotic viruses, such as baculoviruses and retroviruses, adenoviruses and adeno-associated viruses, Herpes viruses, Vaccinia viruses aid all single-stranded, double-stranded, and partially double-stranded DNA viruses, all positive and negative stranded RNA viruses, and replication defective retroviruses. Another example of an expression vector is a yeast artificial chromosome (YAC), which contains both a centromere and two telomeres, allowing YACs to replicate as small linear chromosomes. Another example is a bacterial artificial chromosome (BAC).

The chimeric lipid binding polypeptide fusion proteins of this invention can be expressed in a host cell. As used herein, the term "host cell" refers to any cell or cell line into which a recombinant expression vector for production of a chimeric apolipoprotein fusion protein, as described above, may be transfected for expression. Host cells include progeny of a single host cell, and the progeny may not necessarily be completely identical (in morphology or in total genomic DNA complement) to the original parent cell due to natural, accidental, or deliberate mutation. A host cell includes cells transfected or transformed in vivo with an expression vector as described above. Suitable host cells include, but are not limited to, bacterial cells (e.g. *E. coli*), fungal cells (e.g., *S. cerevisiae*), invertebrate cells (e.g. insect cells such as SF9 cells), and vertebrate cells including mammalian cells.

An expression vector encoding a chimeric lipid binding polypeptide fusion protein can be transfected into a host cell using standard techniques. "Transfection" or "transformation" refers to the insertion of an exogenous polynucleotide into a host cell. The exogenous polynucleotide may be maintained as a non-integrated vector, such as for example a plasmid, or alternatively may be integrated into the host cell genome. Examples of transfection techniques include, but are not limited to, calcium phosphate co-precipitation, DEAE-dextran-mediated transfection, lipofection, electroporation and microinjection. Suitable methods for transfecting host cells can be found in Sambrook et al. (1989) *Molecular Cloning: A Laboratory Manual, 2nd Edition*, Cold Spring Harbor Laboratory press, and other laboratory textbooks. Nucleic acid can also be transferred into cells via a delivery mechanism suitable for introduction of nucleic acid into cells in vivo, such as via a retroviral vector (see e.g., Ferry et al. (1991) *Proc. Natl. Acad. Sci., USA*, 88: 8377-8381; and Kay-etal. (1992) *Human Gene Therapy* 3: 641-647), an adenoviral vector (see, e.g., Rosenfeld (1992) *Cell* 68: 143-155; and Herz and Gerard (1993) *Proc. Natl. Acad. Sci., USA*, 90:2812-2816), receptor-mediated DNA uptake (see e.g., Wu, and Wu (1988) *J. Biol. Chem.* 263: 14621; Wilson et al. (1992) *J. Biol. Chem.* 267: 963-967; and U.S. Pat. No. 5,166,320), direct injection of DNA (see, e.g., Acsadi et al. (1991) *Nature* 332: 815-818; and Wolff et al. (1990) *Science* 247:1465-1468) or particle bombardment (biolistics) (see e.g., Cheng et al. (1993) *Proc. Natl. Acad. Sci., USA*, 90:4455-4459; and Zelenin et al. (1993) *FEBS Letts.* 315: 29-32).

Once expressed, the chimeric lipid binding polypeptides may be purified according to standard procedures of the art, including, but not limited to affinity purification, ammonium sulfate precipitation, ion exchange chromatography, or gel electrophoresis.

In some embodiments, a chimeric lipid binding polypeptide may be produced using a cell free expression system or via solid-state peptide synthesis.

Modified Lipid Binding Polypeptides

In some embodiments of the invention, a lipid binding polypeptide is provided that has been modified such that when the polypeptide is incorporated into a bioactive agent delivery particle as described above, the modification will increase stability of the particle or confer targeting ability. In some embodiments, the modification permits the lipid binding polypeptides of a particle to stabilize the particle's disc shaped structure or conformation. In one embodiment, the modification includes introduction of cysteine residues into apolipoprotein molecules to permit formation of intramolecular or intermolecular disulfide bonds, e.g., by site-directed mutagenesis. In another embodiment, a chemical crosslinking agent is used to form intermolecular links between apolipoprotein molecules to enhance stability of the particles. Intermolecular crosslinking prevents or reduces dissociation of apolipoprotein molecules from the particles and/or prevents displacement by apolipoprotein molecules within an individual to whom the particles are administered.

In other embodiments, a lipid binding polypeptide is modified either by chemical derivatization of one or more amino acid residues or by site directed mutagenesis, to confer targeting ability to or recognition by a cell surface receptor.

Delivery System for Delivery of a Bioactive Agent to an Individual

The invention provides a delivery system for delivery of a bioactive agent to an individual, comprising bioactive agent delivery particles as described above and a carrier, optionally a pharmaceutically acceptable carrier. In some embodiments, the delivery system comprises an effective amount of the bioactive agent.

As used herein, "individual" refers to any prokaryote or eukaryote to which one desires to deliver a bioactive agent. In some embodiments, the individual is a prokaryote such as a bacterium. In other embodiments, the individual is a eukaryote, such as a fungus, a plant, an invertebrate animal, such as an insect, or a vertebrate animal. In some embodiments, the individual is a vertebrate, such as a human, a nonhuman primate, an experimental animal, such as a mouse or rat, a pet animal, such as a cat or dog, or a farm animal, such as a horse, sheep, cow, or pig, a bird (i.e., avian individual), or a reptile (i.e., reptilian individual).

In some embodiments, delivery particles are formulated in a suitable carrier for administration to an individual. As used herein, "carrier" refers to a relatively inert substance that facilitates administration of a bioactive agent. For example, a carrier can give form or consistency to the composition or can act as a diluent. "Pharmaceutically acceptable carriers" refer to carriers that are biocompatible (i.e., not toxic to the host) and suitable for a particular route of administration for a pharmacologically effective substance. Suitable pharmaceutically acceptable carriers include but are not limited to stabilizing agents, wetting and emulsifying agents, salts for varying osmolarity, encapsulating agents, buffers, and skin penetration enhancers. Examples of pharmaceutically acceptable carriers are described in Remington's Pharmaceutical Sciences (Alfonso R. Gennaro, ed., 18th edition, 1990).

As used herein, "effective amount" refers to an amount of a bioactive agent sufficient to effect desired results. A "therapeutically effective amount" or "therapeutic dose" refers to an amount of a bioactive agent sufficient to effect beneficial clinical results, such as for example reduction or alleviation of a symptom of a disease, reduction or alleviation of a fungal or bacterial infection, etc.

In some embodiments, the delivery system is a pharmaceutical composition comprising a bioactive agent delivery particle and a pharmaceutically acceptable carrier. In some embodiments, the pharmaceutical composition comprises a bioactive agent delivery particle that contains a non-polypeptide bioactive agent and a pharmaceutically acceptable carrier. In some embodiments, the bioactive agent delivery particle and the bioactive agent are non-immunogenic when administered to an individual. Immunogenicity may be measured by methods that are well known in the art. For example, immunogenicity may be assessed by an ELISA method, for example by probing serum from an individual to whom bioactive agent delivery particles have been administered for antibody binding to equivalent bioactive agent delivery particles bound to an immunosorbent plate.

Methods of Use

The invention provides methods for administering a bioactive agent to an individual. The methods of the invention include administering a delivery particle as described above that includes a lipid binding polypeptide, a lipid bilayer, and a bioactive agent, wherein the interior of the particle includes hydrophobic surfaces of the lipid bilayer. Optionally, a therapeutically effective amount of the particles is administered, optionally in a pharmaceutically acceptable carrier. Generally, the particles are disc shaped, with a diameter of about 7 to about 29 nm, as measured by native pore limiting gradient gel electrophoresis. Typically, the bioactive agent includes at least one hydrophobic region, which may be integrated into a hydrophobic region of the lipid bilayer.

The route of administration may vary according to the nature of the bioactive agent to be administered, the individual, or the condition to be treated. Where the individual is a mammal, generally administration is parenteral. Routes of administration include, but are not limited to, intravenous, intramuscular, subcutaneous, transmucosal, nasal, intrathecal, topical, and transdermal. In one embodiment, the particles are administered as an aerosol. Delivery particles may be formulated in a pharmaceutically acceptable form for administration to an individual, optionally in a pharmaceutically acceptable carrier or excipient. The invention provides pharmaceutical compositions in the form of delivery particles in a solution for parenteral administration. For preparing such compositions, methods well known in the art may be used, and any pharmaceutically acceptable carriers, diluents, excipients, or other additives normally used in the art may be used.

The delivery particles of the present invention can be made into pharmaceutical compositions by combination with appropriate medical carriers or diluents. For example, the delivery particles can be solubilized in solvents commonly used in the preparation of injectable solutions, such as for example, physiological saline, water, or aqueous dextrose. Other suitable pharmaceutical carriers and their formulations are described in Remington's Pharmaceutical Sciences, supra. Such formulations may be made up in sterile vials containing delivery particles and optionally an excipient in a dry powder or lyophilized powder form. Prior to use, the physiologically acceptable diluent is added and the solution withdrawn via syringe for administration to an individual.

Delivery particles may also be formulated for controlled release. As used herein, "controlled release" refers to release of a bioactive agent from a formulation at a rate that the blood concentration of the agent in an individual is maintained within the therapeutic range for an extended duration, over a time period on the order of hours, days, weeks, or longer. Delivery particles may be formulated in a bioerodible or nonbioerodible controlled matrix, a number of which are well known in the art. A controlled release matrix may include a synthetic polymer or copolymer, for example in the form of a hydrogel. Examples of such polymers include polyesters, polyorthoesters, polyanhydrides, polysaccharides, poly (phosphoesters), polyamides, polyurethanes, poly(imidocarbonates) and poly(phosphazenes), and poly-lactide-co-glycolide (PLGA), a copolymer of poly(lactic acid) and poly (glycolic acid). Collagen, albumin, and fibrinogen containing materials may also be used.

Delivery particles may be administered according to the methods described herein to treat a number of conditions including, but not limited to, bacterial infections, fungal infections, disease conditions, metabolic disorders, or as a prophylactic medication, for example to prevent a bacterial or fungal infection (e.g., pre- or post-surgically). Delivery particles may be used, for example, to deliver an anti-tumor agent (e.g., chemotherapeutic agent, radionuclide) to a tumor. In one embodiment, the lipid binding polypeptide includes a moiety that targets the particle to a particular tumor. Delivery particles may also be used for administration of nutraceutical substances, i.e., a food or dietary supplement that provides health benefits. In some embodiments, delivery particles are co-administered with other conventional therapies, for example, as part of a multiple drug "cocktail," or in combination with one or more orally administered agents, for example, for treatment of a fungal infection. Delivery particles may also be administered as insecticides or herbicides.

In one aspect, the invention provides a method for treating a fungal infection in an individual. The method includes administering a therapeutically effective amount of an anti-fungal agent in a pharmaceutically acceptable carrier to the individual, wherein the anti-fungal agent is incorporated into a particle that includes a lipid binding polypeptide and a lipid bilayer, wherein the interior of the lipid bilayer is hydrophobic. In one embodiment, the anti-fungal agent is AmB, incorporated into the hydrophobic interior of the lipid bilayer. In some embodiments, the lipid binding polypeptide is a chimeric protein that includes a targeting moiety and/or a moiety with biological activity. In one embodiment, the lipid binding polypeptide includes the targeting moiety yeast α-mating factor peptide. In another embodiment, the lipid binding polypeptide includes the anti-microbial peptide histatin 5.

In another aspect, the invention provides a method for treating a tumor in an individual. The method includes administering a therapeutically effective amount of a chemotherapeutic agent in bioactive agent delivery particles as described above, in a pharmaceutically acceptable carrier. In one embodiment, the chemotherapeutic agent is camptothecin. A lipid binding polypeptide component of the delivery particles may include a targeting moiety to target the particles to tumor cells. In one embodiment, vasoactive intestinal peptide (VIP) is attached to the lipid binding polypeptide. Since breast cancer cells often overexpress the VIP receptor, in one embodiment, bioactive agent delivery particles comprising camptothecin and lipid binding polypeptide-VIP chimeras are used in a method of treatment for breast cancer.

Targeting

A delivery particle of the invention may include a targeting functionality, for example to target the particles to a particular cell or tissue type, or to the infectious agent itself. In some embodiments, the particle includes a targeting moiety attached to a lipid binding polypeptide or lipid component. In some embodiments, the bioactive agent that is incorporated into the particle has a targeting capability.

In some embodiments, by engineering receptor recognition properties into a lipid binding polypeptide, such as an apolipoprotein molecule, the particles can be targeted to a specific cell surface receptor. For example, bioactive agent delivery particles may be targeted to a particular cell type known to harbor a particular type of infectious agent, for example by modifying the lipid binding polypeptide component of the particles to render it capable of interacting with a receptor on the surface of the cell type being targeted.

In one aspect, a receptor-mediated targeting strategy may be used to deliver antileishmanial agents to macrophages, which are the primary site of infection for protozoal parasites from the genus *Leishmania*. Examples of such species include *Leishmania major, Leishmania donovani*, and *Leishmania braziliensis*. Bioactive agent delivery particles containing an antileishmanial agent may be targeted to macrophages by altering the lipid binding polypeptide component of the particles to confer recognition by the macrophage endocytic class A scavenger receptor (SR-A). For example, an apolipoprotein which has been chemically or genetically modified to interact with SR-A may be incorporated into delivery particles that contain one or more bioactive agents that are effective against *Leishmania* species, such as, for example, AmB, a pentavalent antimonial, and/or hexadecylphosphocholine. Targeting of delivery particles that contain an antileishmanial agent specifically to macrophages may be used as a means of inhibiting the growth and proliferation of *Leishmania* spp.

In one embodiment an SR-A targeted bioactive agent delivery particle containing AmB is administered to an individual in need of treatment for a leishmanial infection. In another embodiment, another antileishmanial agent, such as hexadecylphosphocholine is administered prior, concurrently, or subsequent to treatment with the AmB containing-particles.

In some embodiments, targeting is achieved by modifying a lipid binding polypeptide, such as an apolipoprotein, to be incorporated into the bioactive agent delivery particle, thereby conferring SR-A binding ability to the particle. In some embodiments, targeting is achieved by altering the charge density of the lipid binding polypeptide by chemically modifying one or more lysine residues, for example with malondialdehyde, maleic anhydride, or acetic anhydride at alkaline pH (see, e.g., Goldstein et al. (1979) *Proc. Natl. Acad. Sci.* 98:241-260). In one embodiment, Apo B-100 or a truncated form thereof, such as the N-terminal 17% of ApoB-100 (residues 1-782 of apoB-17), is modified by reaction with malondialdehyde. In other embodiments, an apolipoprotein molecule, such as any of the apolipoproteins described herein, may also be chemically modified by, for example acetylation or maleylation, and incorporated into a bioactive agent delivery particle containing an antileishmanial agent.

In other embodiments, SR-A binding ability is conferred to a delivery particle by modifying the lipid binding polypeptide by site directed mutagenesis to replace one or more positively charged amino acids with a neutral or negatively charged amino acid.

In other embodiments, SR-A recognition is conferred by preparing a chimeric lipid binding polypeptide that includes an N- or C-terminal extension having a ligand recognized by SR-A or an amino acid sequence with a high concentration of negatively charged residues. A negatively charged polypeptide extension would not be attracted to the lipid surface of the bioactive agent delivery particle, thereby rendering it more accessible to the ligand binding site of the receptor.

Methods for Preparing Bioactive Agent Delivery Particles

The invention provides methods for formulating a bioactive agent delivery particle. In one embodiment, a process is provided that includes adding lipid binding polypeptide molecules to a mixture that includes bilayer-forming lipids and bioactive agent molecules.

In some embodiments, the lipid-bioactive agent mixture also includes a detergent, such as for example sodium cholate, cholic acid, or octyl glucoside, and the process further includes removing the detergent after the lipid binding polypeptide has been added. Typically, the detergent is removed by dialysis or gel filtration. In one embodiment, the process includes combining bilayer-forming lipids and bioactive agent molecules in a solvent to form a-bioactive agent mixture, drying the mixture to remove the solvent (e.g., under a stream of $N_2$ and/or by lyophilization), contacting the dried mixture with a solution that includes a detergent to form a lipid-bioactive agent-detergent mixture, adding lipid binding polypeptide molecules to this mixture, and then removing the detergent.

In some embodiments, the particles are prepared using a microfluidizer processor. This procedure employs high pressure, forcing the components together in a reaction chamber.

In some embodiments, the particles are prepared by incubation of a suspension of lipid vesicles containing a bioactive agent in the presence of a lipid binding polypeptide, such as an apolipoprotein. In one embodiment, the suspension is sonicated.

In other embodiments, delivery particles are prepared from a pre-formed vesicle dispersion. Lipids, e.g., phospholipids, are hydrated with buffer and dispersed by agitation or sonication. To the dispersion of lipid bilayer vesicles, solubilized bioactive agent is added in a suitable solvent to form a lipid-bioactive agent complex. In some embodiments, the solvent is volatile or dialyzable for convenient removal after addition of bioactive agent to the lipid bilayer vesicle dispersion. Following further agitation, lipid binding polypeptide is added and the sample is incubated, mixed by agitation, and/or sonicated. Typically, the vesicles and apolipoprotein are incubated at or near the gel to liquid crystalline phase transition temperature of the particular bilayer forming lipid or mixture of bilayer-forming lipids being used. The phase transition temperature may be determined by calorimetry.

Preferably, a suitable bilayer-forming lipid composition is used such that, upon dispersion in aqueous media, the lipid vesicles provide a suitable environment to transition a bioactive agent from a carrier solvent into an aqueous milieu without precipitation or phase separation of the bioactive agent. The pre-formed lipid bilayer vesicles are also preferably capable of undergoing lipid binding polypeptide-induced transformation to form the delivery particles of the invention. Further, the lipid-bioactive agent complex preferably retains properties of the lipid vesicles that permit transformation into bioactive agent delivery particles upon incubation with a lipid binding polypeptide under appropriate conditions. The unique combination of lipid substrate-bioactive agent complex organization and lipid binding polypeptide properties combine to create a system whereby, under appropriate conditions of pH, ionic strength, temperature, and lipid-bioactive agent-lipid binding polypeptide concentration, a ternary structural reorganization of these materials occurs wherein stable lipid binding polypeptide circumscribing lipid bilayers are created with a bioactive agent incorporated into the lipid milieu of the bilayer. For a discussion of the effect of pH, ionic strength and lipid binding polypeptide concentration on the ability of lipid binding polypeptides to induce transformation of different types of phospholipid vesicles into disc shaped particles, see Weers et al. (2001) *Eur. J. Biochem.* 268:3728-35.

The particles prepared by any of the above processes may be further purified, for example by dialysis, density gradient centrifugation and/or gel permeation chromatography.

In a preparation method for formation of bioactive agent delivery particles, preferably at least about 70, more preferably at least about 80, even more preferably at least about 90, even more preferably at least about 95 percent of the bioactive agent used in the procedure is incorporated into the particles.

The invention provides bioactive agent delivery particles prepared by any of the above methods. In one embodiment, the invention provides a pharmaceutical composition comprising a delivery particle prepared by any of the above methods and a pharmaceutically acceptable carrier.

Storage and Stability

Figure 5:
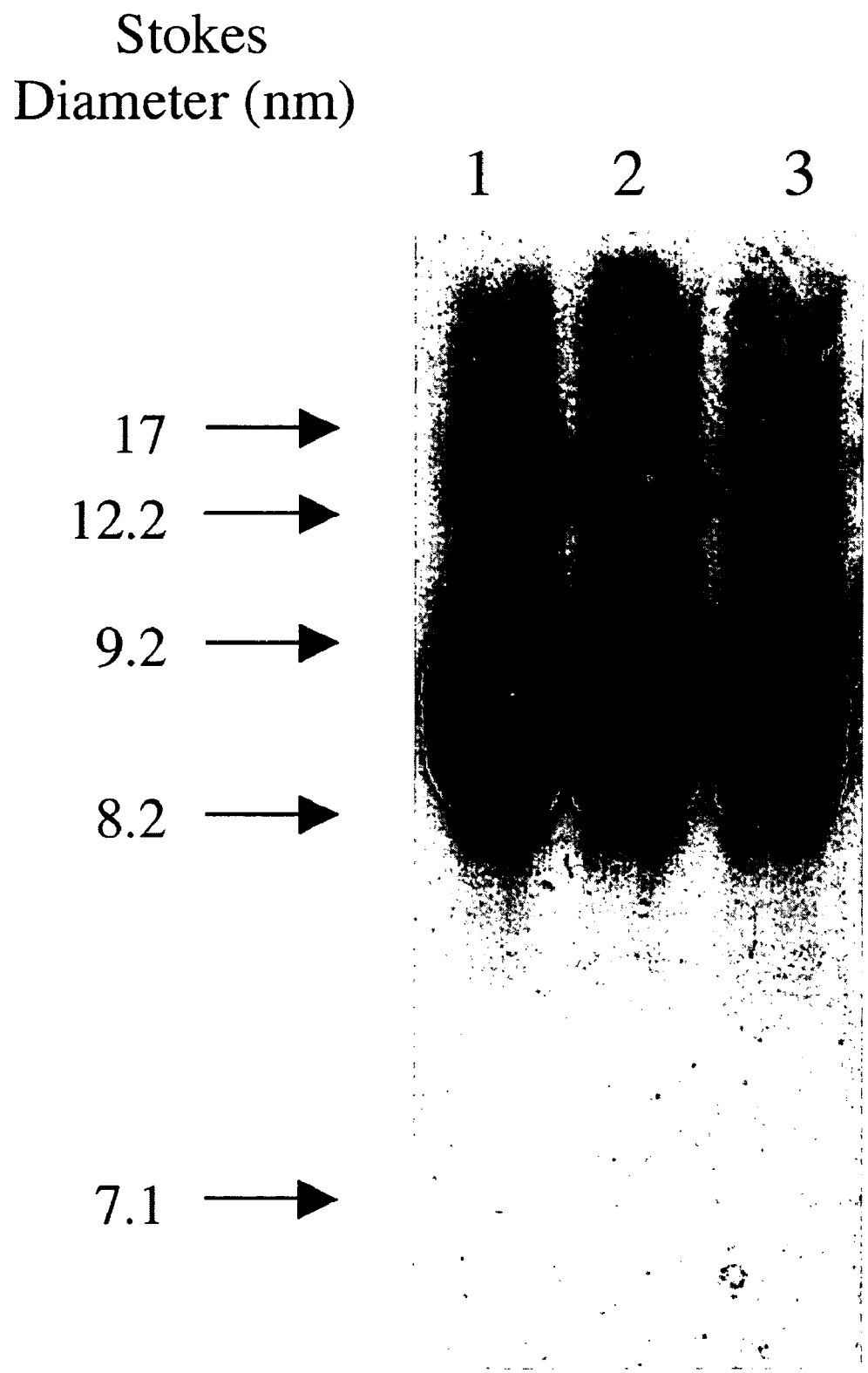
FIG. 5 depicts a comparison of effects of different storage conditions on the size and structural integrity of Apolipoprotein E N-terminal domain (ApoE3NT)-DMPC/DMPG-AmB particle stability. Particles were isolated by density ultracentrifugation and then subjected to electrophoresis on a native PAGE 4-20% gradient slab gel. The gel was stained with Amido Black. Lane 1: particles stored in phosphate buffer at 4° C. for 24 hours; Lane 2: particles stored in phosphate buffer at −20° C. for 24 hours; Lane 3: particles lyophilized and frozen at −80° C. for 24 hours, and then redissolved in $H_2O$. The relative migration of size standards is shown on the left.

Particles of the invention are stable for long periods of time under a variety of conditions (see, for example, FIG. 5). Particles, or compositions comprising particles of the invention, may be stored at room temperature, refrigerated (e.g., about 4° C.), or frozen (e.g., about −20° C. to about −80° C.). They may be stored in solution or dried (e.g., lyophilized). Bioactive agent delivery particles may be stored in a lyophilized state under inert atmosphere, frozen, or in solution at 4° C. Particles may be stored in a liquid medium, such as a buffer (e.g., phosphate or other suitable buffer), or in a carrier, such as for example a pharmaceutically acceptable carrier, for use in methods of administration of a bioactive agent to an individual. Alternatively, particles may be stored in a dried, lyophilized form and then reconstituted in liquid medium prior to use.

Kits

The reagents and particles described herein can be packaged in kit form. In one aspect, the invention provides a kit that includes delivery particles and/or reagents useful for preparing delivery particles, in suitable packaging. Kits of the invention include any of the following, separately or in combination: lipid binding polypeptides (e.g., apolipoproteins), phospholipids, bioactive agents, vectors, reagents, enzymes, host cells and/or growth medium for cloning and/or expression of recombinant lipid binding polypeptides (e.g., recombinant apolipoproteins) and/or lipid binding polypeptide chimeras (e.g., apolipoprotein chimeras), and reagents and/or pharmaceutically acceptable carriers for formulating delivery particles for administration to an individual.

Each reagent or formulation is supplied in a solid form, liquid buffer, or pharmaceutically acceptable carrier that is suitable for inventory storage, or optionally for exchange or addition into a reaction, culture, or injectable medium. Suitable packaging is provided. As used herein, "packaging" refers to a solid matrix or material customarily used in a system and capable of holding within fixed limits one or more of the reagents or components (e.g., delivery particles) for use in a method for delivery of a bioactive agent or one or more reagents for preparing or formulating delivery particles (e.g., apolipoprotein molecules, phospholipids, bioactive agents). Such materials include, but are not limited to, glass and plastic (e.g., polyethylene, polypropylene, and polycarbonate) bottles, vials, paper, plastic, and plastic-foil laminated envelopes, and the like.

A kit may optionally provide additional components that are useful in the methods and formulation procedures of the invention, such as buffers, reacting surfaces, or means of purifying delivery particles.

In addition, the kits optionally include labeling and/or instructional or interpretive materials providing directions (i.e., protocols) for the practice of the methods of this invention, such as preparation, formulation and/or use of delivery particles. While the instructional materials typically comprise written or printed materials they are not limited to these formats. Any medium capable of storing such instructions and communicating them to an end user is contemplated by this invention. Such media include, but are not limited to, electronic storage media (e.g., magnetic discs, tapes, cartridges, chips), optical media (e.g., CD ROM), and the like. Such media may include addresses to Internet sites that provide such instructional materials.

The following examples are intended to illustrate but not limit the invention.

EXAMPLES

Example 1

Preparation and Characterization of ApoA-I-Phospholipid-Amphotericin B Particles Preparation of Recombinant ApoA-I Recombinant Apo-A-I was prepared as described in Ryan et al. (2003) *Protein Expression and Purification* 27:98-103, and was used to prepare Apo-A-1-phospholipid-AmB particles, as described below.

Preparation of ApoA-I-phospholipid-AmB Particles

ApoA-I-phospholipid-AmB particles were prepared as follows:

A 7:3 molar ratio of dimyristoylphosphatidylcholine (DMPC) and dimyristoylphosphatidylglycerol (DMPG) were dissolved in chloroform:methanol (3:1, v/v). To 10 mg of the DMPC/DMPG mixture, 0.25 ml of AmB (2 mg/ml; solubilized in acidified chloroform:methanol (3:1, v/v)) was added. The mixture was dried under a stream of $N_2$ gas to create a thin film on the vessel wall. The dried sample was then subjected to lyophilization for sixteen hours to remove traces of solvent.

The dried lipid mixture was resuspended in 0.5 ml Tris-Saline buffer (10 mM Tris base 150 mM NaCl, pH 8), and the mixture was vortexed for 30 seconds.

To the resuspended lipid mixture, 0.5 ml of 22 mM sodium cholate was added to the mixture and vortexed for 3 minutes. This mixture was incubated at 37° C. with vortexing every 10 minutes for 1.25 hours or until the mixture was clear. To the cleared solution, 2 ml of isolated recombinant ApoA-I, prepared as described in Example 1, was added at a concentration of 1.5 mg/ml, and the mixture was incubated at 37° C. for an additional 1 hour. To remove sodium cholate, the sample was subjected to dialysis against 4 liters of Tris-Saline at 4° C. for 72 hours with a change of dialysis buffer every 24 hours.

The sample was further purified by density gradient ultracentrifugation. The solution was adjusted to a density of 1.30 g/ml by the addition of solid KBr in 1.5 ml. The sample was transferred to a 3 ml centrifuge tube, overlayered with saline and centrifuged at 275,000×g for 3 hours in a Beckman L7-55 centrifuge.

Particle Stability

The particles prepared according to this procedure were stable for more than 3 months in lyophilized form.

Characterization of Particles

Figure 1:
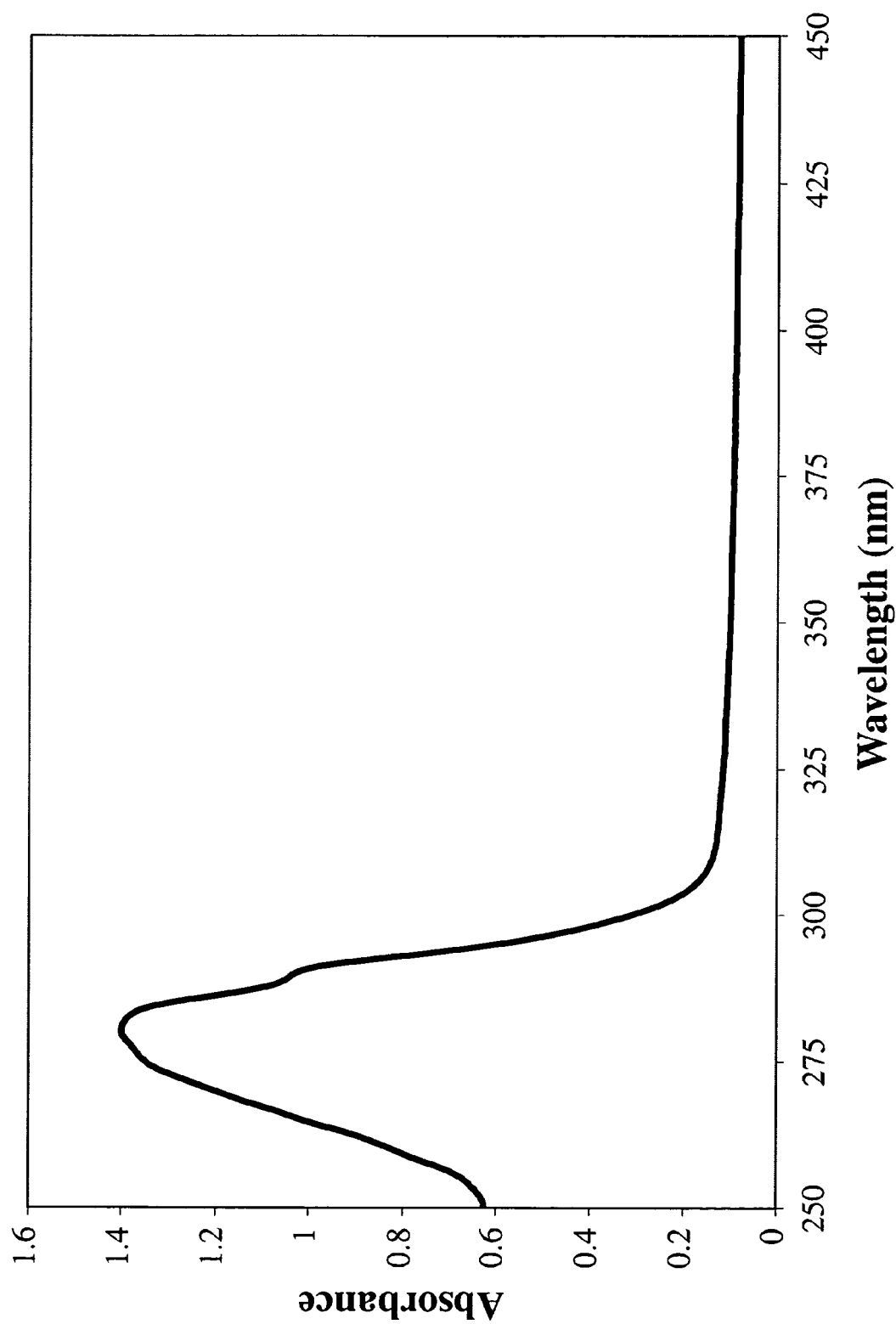
FIG. 1 depicts a UV/visible absorbance spectrum, from 250-450 nm, of ApoA-I-phospholipid particles without a bioactive agent, prepared as in Example 1.
Figure 2:
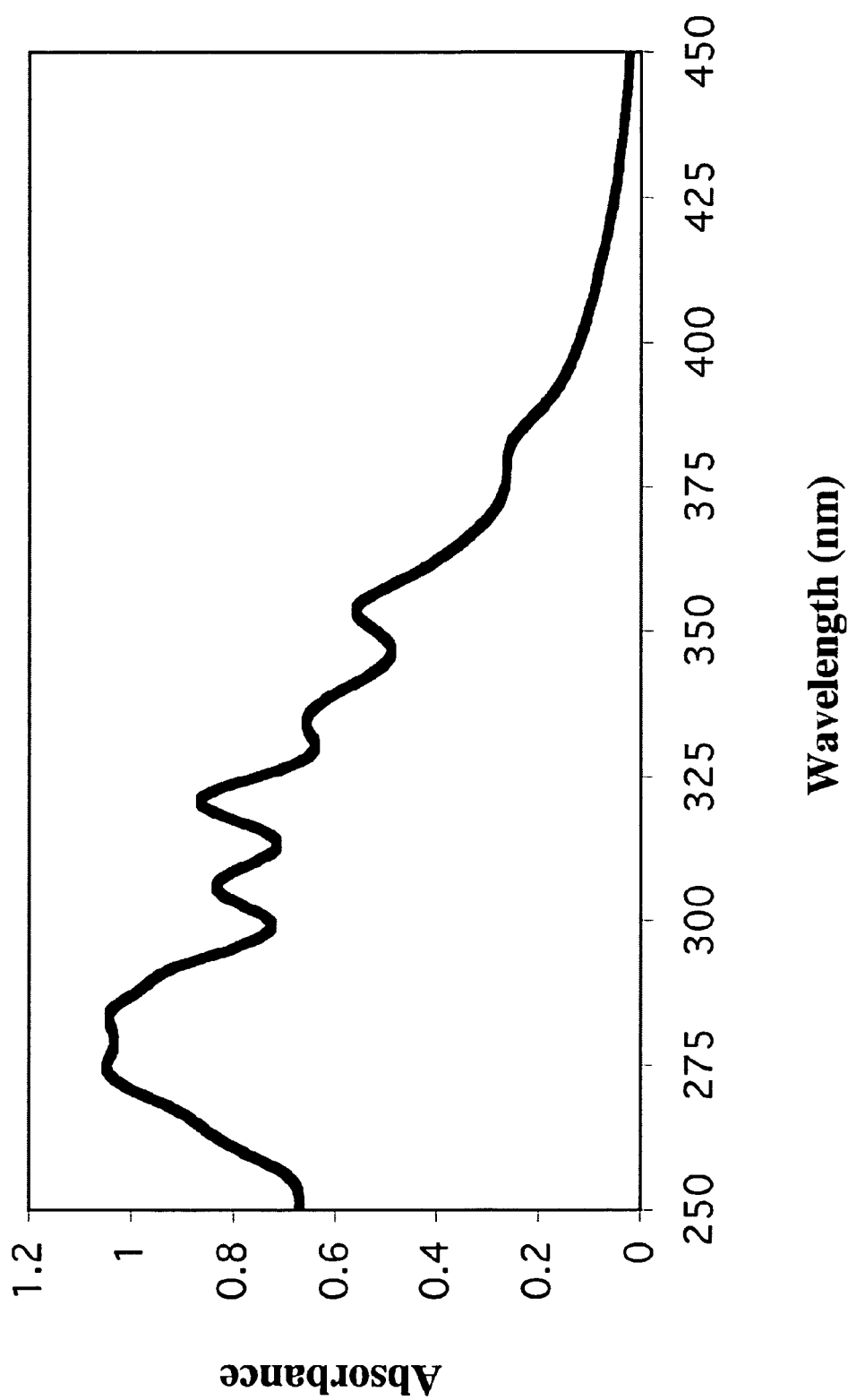
FIG. 2 depicts a UV/visible absorbance spectrum, from 250-450 nm, of ApoA-I-phospholipid-AmB particles, prepared as in Example 1.

UV/visible scans were performed for ApoA-I-phospholipid particles, prepared as described above but without the addition of AmB, and were compared with scans for the AmB-containing particles. FIG. 1 shows the scan for particles that do not include AmB. The only peak observed was a protein peak at around 280 nm. FIG. 2 shows the scan for AmB-containing particles prepared as described above. In addition to the peak at around 280 nm, a number of additional peaks were observed in the 300-400 nm region of the spectrum, confirming the presence of AmB. Free AmB is insoluble in aqueous media and has different spectral properties than observed in FIG. 2. Madden et al. (1990) *Chemistry and Physics of Lipids*, 52:189-98.

Figure 3:
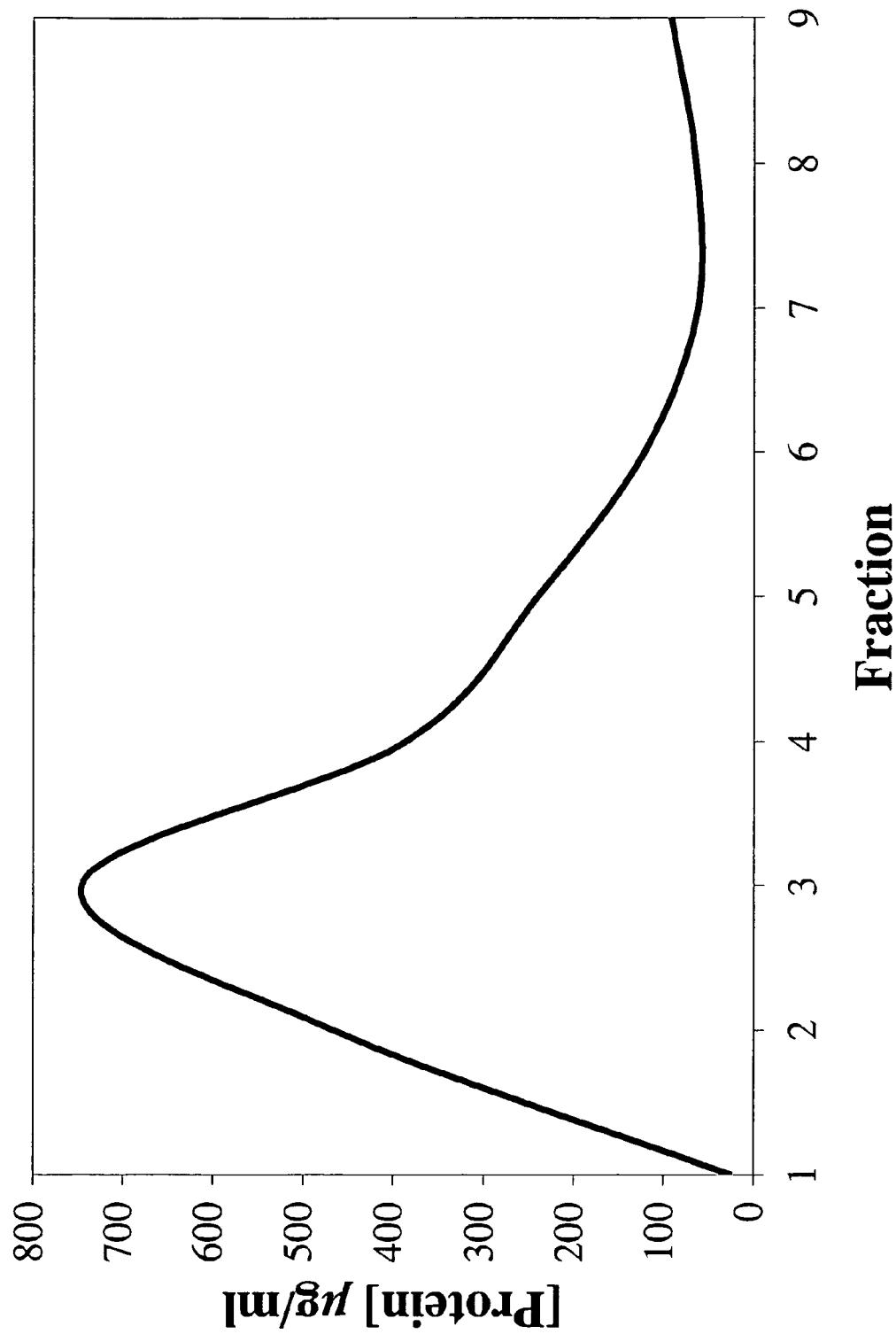
FIG. 3 depicts a plot of fraction number versus protein concentration for ApoA-I-phospholipid-AmB particles after density gradient ultracentrifugation. Particles were prepared as described in Example 2 and adjusted to 1.3 g/ml density by the addition of KBr. The solution was centrifuged in a discontinuous gradient for 5 hours at 275,000×g at 110° C. Following centrifugation, the tube contents were fractionated from the top and the protein content in each fraction determined.

Characterization studies revealed that the ApoA-I, phospholipid, and AmB migrate as a discrete particle population when subjected to density gradient ultracentrifugation (FIG. 3). The complexes float to a characteristic density in the gradient that is dependent upon the protein/lipid ratio in the particles.

Figure 4:
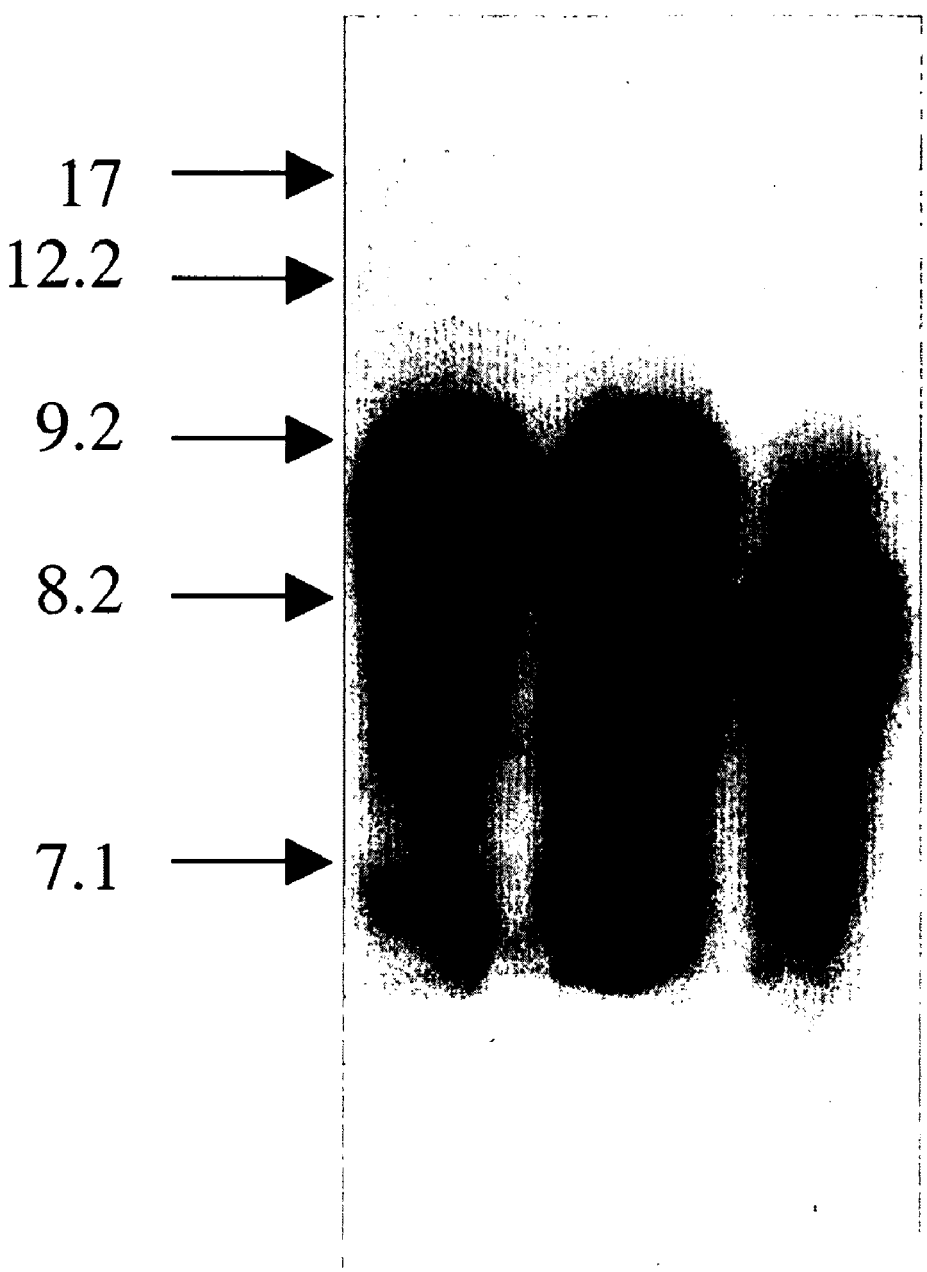
FIG. 4 depicts a native polyacrylamide gel electrophoresis (PAGE) analysis of ApoA-I-phospholipid particles, on a 4-20% acrylamide gradient slab gel. Particles were prepared with ApoA-I and two different lipid preparations, DMPC/DMPG or palmitoyloleylphosphatidylcholine (POPC). The gel was stained with Coomassie Blue. Lane 1: ApoA-I-POPC particles; Lane 2: ApoA-I-POPC-AmB particles; Lane 3: ApoA-I-DMPC/DMPG-AmB particles. The relative migration of size standards is shown on the left.

Further, gradient gel electrophoresis under non-denaturing conditions revealed that the major complex generated is of uniform size, displaying a Stokes' diameter of 8.5 nm (FIG. 4). Analysis of the isolated particles revealed that significant deviation from the original molar ratios of AmB, phospholipid, and apolipoprotein did not occur.

Example 2

Antifungal Activity of AmB Containing Bioactive Agent Delivery Particles Against *Saccharomyces cerevisiae*

ApoA-I-DMPC/DMPG-AmB particles were prepared as described in Example 1 and used to determine antifungal activity of the complexes. Cultures of *S. cerevisiae* were grown in YPD medium in the presence of varying amounts of ApoA-I-DMPC/DMPG-AmB particles (0-25 μg AmB/ml). The cultures were grown for 16 hours at 30° C., and the extent of culture growth monitored spectrophotometrically. As shown in FIG. 8, the AmB-containing particles were extremely effective in inhibiting fungal growth in a dose-dependent manner.

Example 3

Long Term Stability of Bioactive Agent Delivery Particles

Recombinant ApoE3NT-terminal domain (ApoE3NT) was prepared as in Fisher et al. (1997) *Biochem Cell Biol* 75:45-53. ApoE3NT-AmB-containing particles were prepared via the cholate dialysis method described in Example 1, and used to assess long-term stability.

FIG. 5 shows a native PAGE 4-20% gradient slab gel of particles stored in phosphate buffer at 4° C. (lane 1), stored in phosphate buffer at −20° C. (lane 2), or frozen in phosphate buffer at −80° C., lyophilized, and redissolved in $H_2O$ prior to analysis. The size and mobility of the AmB-containing particles were unaffected by freezing and thawing, or by lyophilization and resolubilization, indicating that the particles retained their integrity under these conditions. These are important parameters with regard to scale up and long-term storage of AmB delivery particles.

Example 4

Preparation of AmB-Containing Bioactive Agent Delivery Particles with POPC

ApoA-I-POPC particles were prepared using the cholate dialysis method described in Example 1. A native PAGE gradient gel analysis of ApoA-I-POPC particles is shown in FIG. 4. Particles without AmB are shown in lane 1 and particles with AmB are shown in lane 2. The gel indicates that incorporation of AmB into the particles does not alter their size. However, the gel indicates that the POPC containing particles are a different size than DMPC/DMPG particles, shown in lane 3.

Example 5

Preparation of AmB-Containing Particles with a Microfluidizer Processor

ApoA-I, AmB, egg PC, DPPG, and cholesterol were combined in a microfluidizer sample holder and passed through the reaction chamber of microfluidizer processor at 18,000 psi. The resultant solution was collected and characterized in terms of particle formation, incorporation of hydrophobic substances, size, and stability. AmB-containing particles of about 16 nm diameter were obtained, which were stable to lyophilization and aqueous solvent reconstitution.

Example 6

Preparation of AmB-Containing Particles from Phospholipid Vesicles

A suspension of AmB-containing phospholipid vesicles was prepared by adding an aliquot of a 20-40 mg/ml solution of AmB in DMSO, corresponding to 2.5 mg AmB, to a preformed phospholipid aqueous dispersion containing a molar ratio of 7:3 DMPC:DMPG. The vesicles were incubated at the gel to liquid phase transition temperature of the phospholipids (about 24° C.). Addition of 4 mg apolipoprotein led to a time-dependent decrease in sample turbidity, consistent with formation of AmB-containing bioactive agent delivery particles. Full sample clarity was achieved by mild bath sonication at 21-25° C. for 1-20 minutes or in 4-16 hours without sonication at 24° C. The resulting particles exhibited >90% AmB incorporation efficiency, i.e., the percentage of AmB starting material that is recovered in delivery particles, and no material was lost upon filtration, centrifugation, or dialysis. Other tests revealed that similar results can be achieved with AmB concentration adjusted to as high as 5 mg/10 mg phospholipid. This procedure worked equally well with any of five apolipoproteins tested (ApoA-I, ApoE3NT, *Bombyx mori*

ApoIII, and a variant form of human ApoA-I that includes a C-terminal extension including the antifungal peptide, Histatin 5, and a variant form of human ApoA-I that includes a C-terminal extension including the *S. cerevisiae* α-mating factor peptide).

Density gradient ultracentrifugation of ApoA-I or ApoE3NT containing particles revealed a single population of particles that floated to a characteristic density in the range of 1.21 g/ml, consistent with formation of lipid-protein complexes. Characterization of the fractions obtained following density gradient ultracentrifugation revealed that phospholipid, AmB, and apolipoprotein migrated to the same position in the gradient, consistent with formation of AmB-containing particles.

Comparison of the relative migration of ApoA-I-AmB-containing particles with known standards on native PAGE indicated that over 90% of the particles had a Stokes' diameter of approximately 8.5 nm. This value is similar to particles generated in the absence of AmB, indicating that addition of this bioactive agent did not significantly alter the size distribution of the particles.

As a measure of the overall stability of the ApoA-I-AmB-containing bioactive agent delivery particles, the particles were frozen at −20° C. or lyophilized. Freezing/thawing had no effect on the size distribution of the particles. Likewise, subjecting the particles to lyophilization and re-dissolving in $H_2O$ did not affect the size distribution or sample appearance.

These data strongly suggest that AmB, phospholipids, and apolipoprotein combined to form a homogeneous population of bioactive agent delivery particles in which AmB is fully integrated into the bilayer portion of the particle. Spectrophotometric analysis of the AmB-containing particles revealed a characteristic set of peaks in the visible range that are consistent with AmB solubilization in the bioactive agent delivery particle.

Example 7

Comparison of AmB-Containing Particles Prepared as in Example 6 with Particles Prepared by an Alternate Procedure Incorporation of bioactive agent into bioactive agent delivery particles using the method described in Example 6 was compared with incorporation into "neo-HDL" particles prepared according to Shouten et al. (1993) *Molecular Pharmacology* 44:486-492, as follows: Three mg of egg yolk phosphatidylcholine, 0.9 mg cholesterol, and 1.5 mg AmB, dissolved in chloroform, were mixed in a 20 ml glass vial, and the solvent was evaporated under a stream of nitrogen. Ten ml of sonication buffer (10 mM Tris HCl, pH 8.0, 100 mM KCl, 1 mM EDTA, and 0.025% $NaN_3$), degassed and saturated with nitrogen, were added and the contents of the vial sonicated with a Macrotip (14 µm average output) under a stream of nitrogen. The temperature was maintained above 41° C. and below 50° C. The sonication was stopped after 60 minutes, and the temperature adjusted to 42° C. Sonication was continued and 20 mg of ApoA-I, dissolved in 2 ml of 4M urea, was added in ten equal portions over a period of 10 minutes. After all of the protein was added, sonication was continued for 30 min at 42° C.

Figure 12:
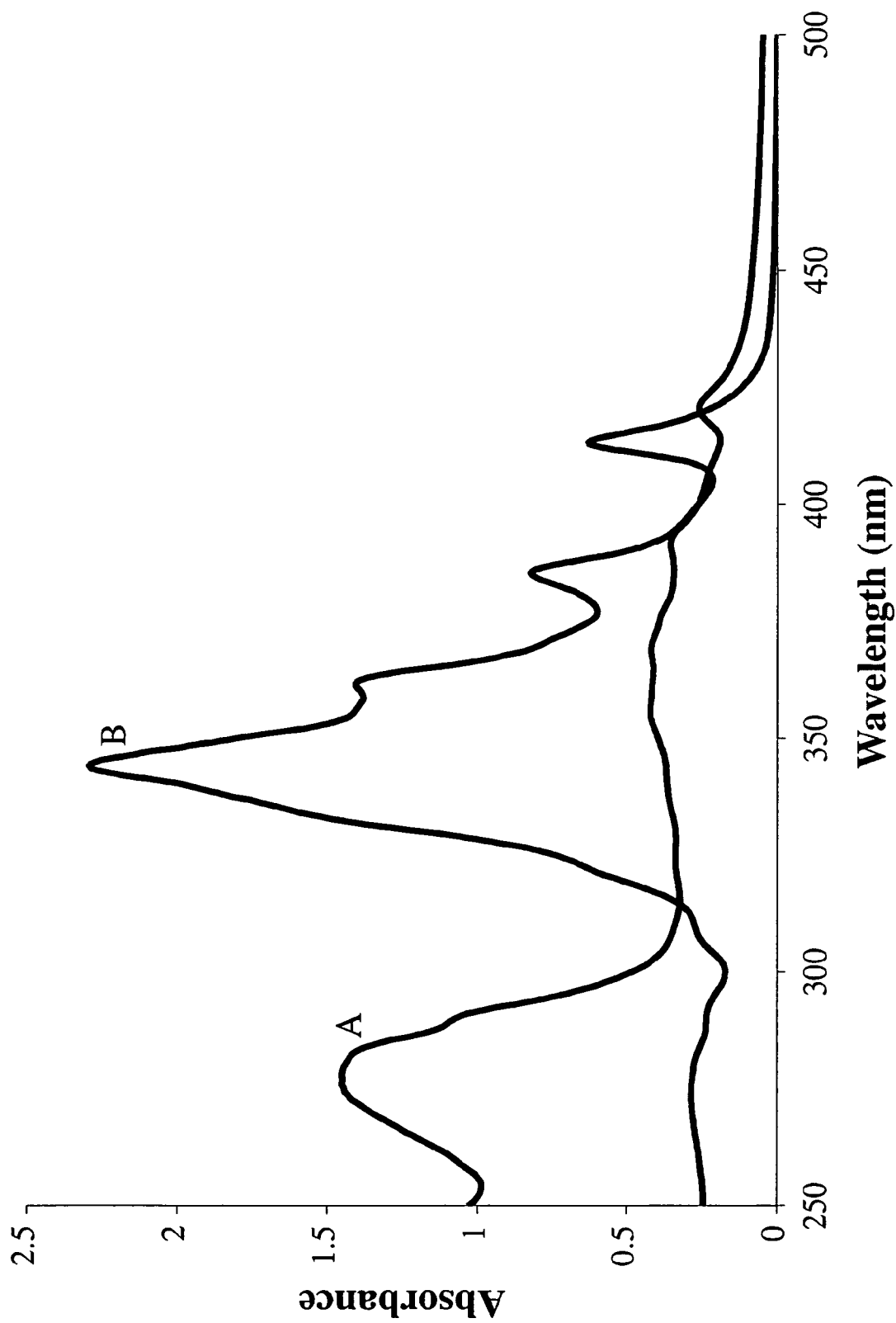
FIG. 12 depicts a UV/visible spectral comparison of AmB incorporation into lipid particles prepared as described in Example 7 (FIG. 12A) and bioactive agent delivery particles prepared as described in Example 6 (FIG. 12B).
Figure 13:
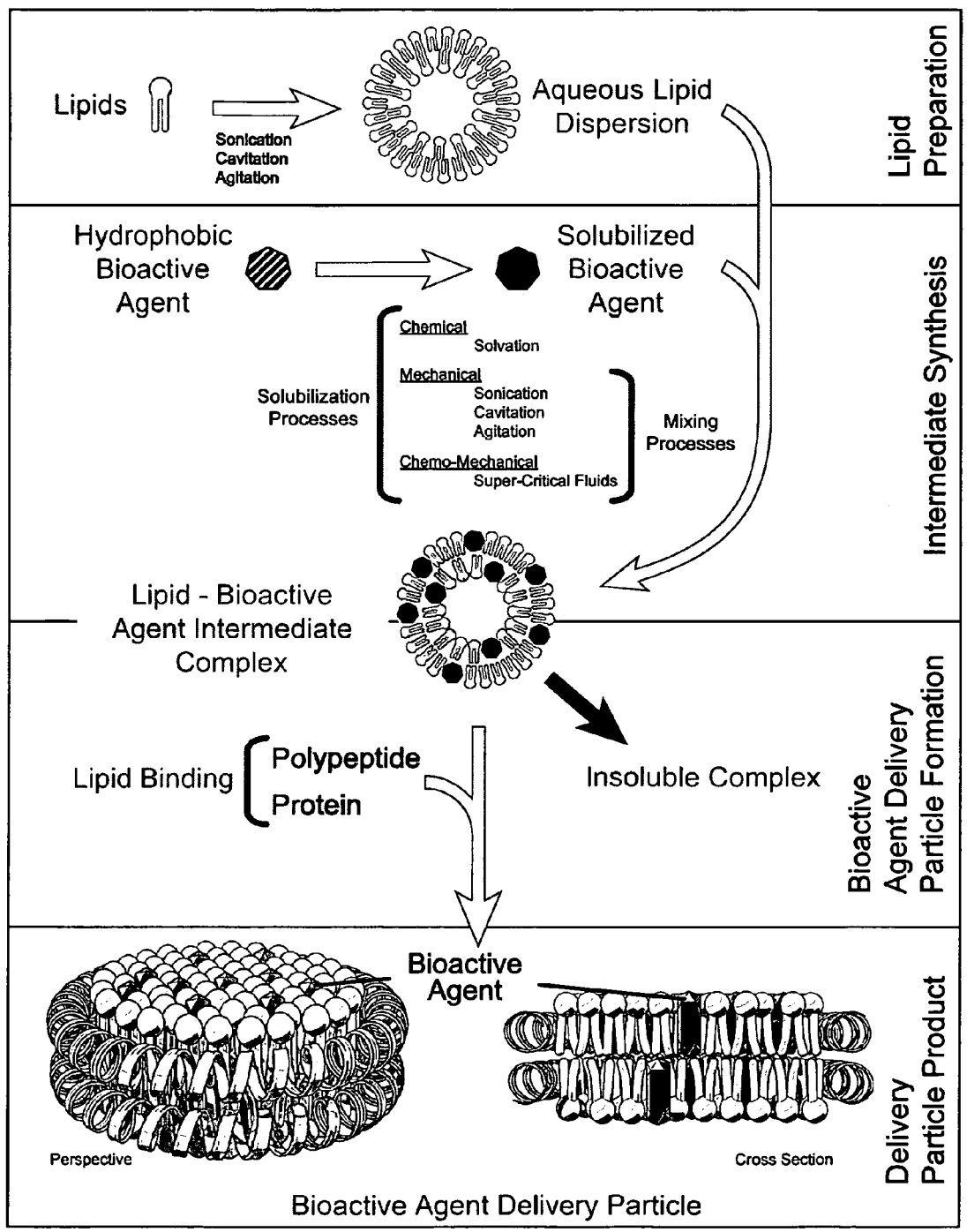
FIG. 13 is an illustration of an embodiment of a bioactive agent delivery particle preparation procedure.

The sonication mixture was then centrifuged for 3 minutes to remove large particles and insoluble material and the supernatant analyzed by UV/Visible spectrophotometry to assess the amount of amphotericin B solubilized in the product particles. It was noted that the solution was slightly opaque. The sample was scanned from 250 nm to 500 nm. For comparison, AmB-containing particles prepared by the procedure described in Example 6 were examined. The results are shown in FIG. 12. The region of the spectrum arising from AmB (300-500 nm) is quite distinct between the two samples. Whereas AmB-containing bioactive agent delivery particles generated using the protocol described in Example 6 had strong characteristic absorbance maxima that indicate solubilization and incorporation of AmB into the particles (Madden et al., supra) (FIG. 12B), the sample prepared according to Schouten et al. did not give rise to these characteristic spectral maxima (FIG. 12A). Indeed, the spectrum obtained is very similar to that reported by Madden et al., supra, for an aqueous dispersion of AmB in the absence of lipid. Thus, AmB was not incorporated into lipid particles using this procedure, whereas the procedure described in Example 6 resulted in significant AmB incorporation.

Example 8

Figure 10:
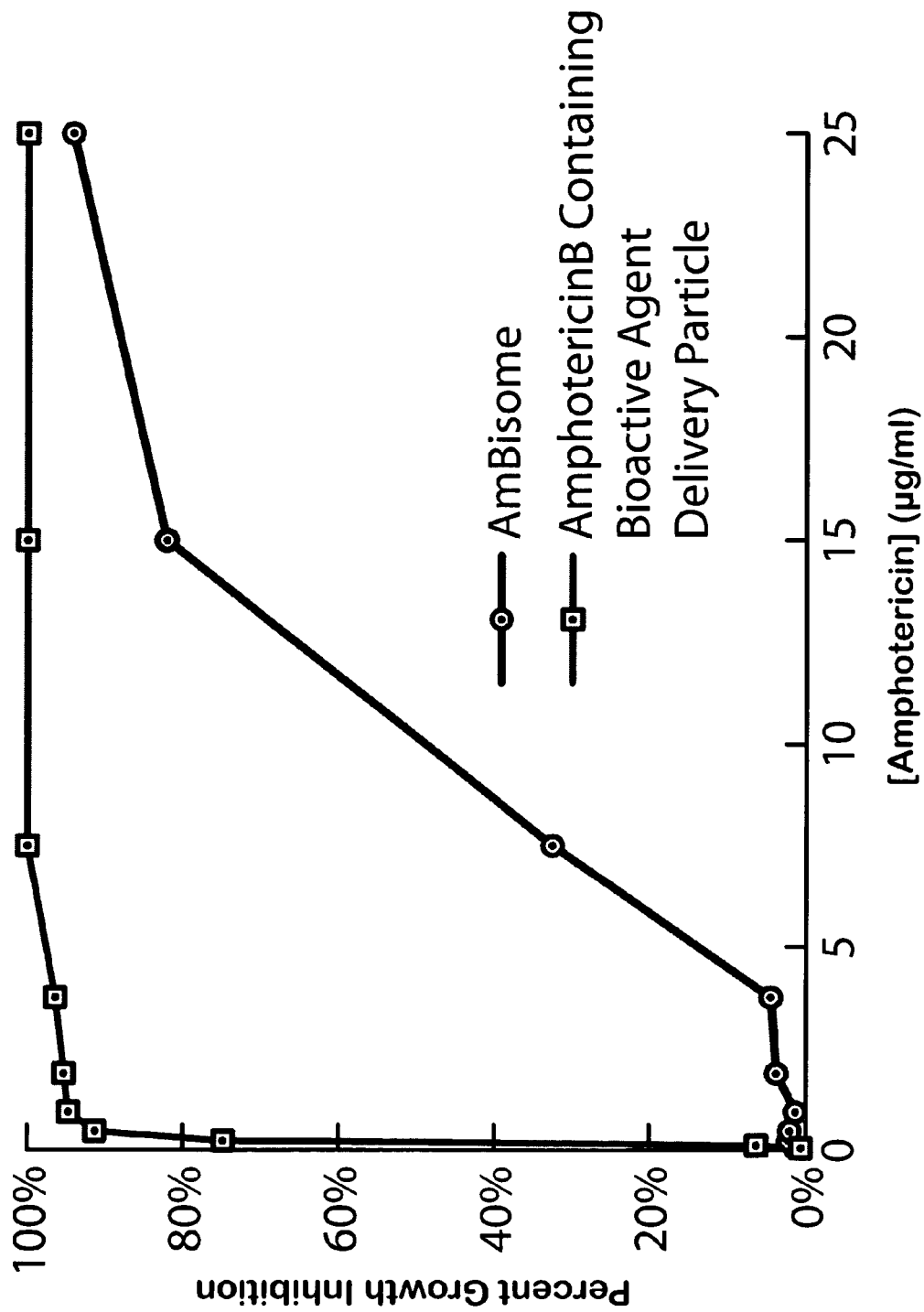
FIG. 10 shows a comparison between the ability of ApoA-I-DMPC/DMPG-AmB particles and AmBisome® to inhibit growth of *S. cerevisiae*, as described in Example 8.

Comparison of Anti-Fungal Activity of AmB-Containing Bioactive Agent Delivery Particles with Liposomal AmB Formulation Anti-fungal activity of ApoA-I-AmB particles, prepared as in Example 6, and a commercial liposomal formulation of AmB, AmBisome®, were compared with respect to their ability to inhibit the growth of the yeast, *S. cerevisiae*. The data in FIG. 10 show that Apo-A-I-AmB bioactive agent delivery particles more effectively inhibited *S. cerevisiae* growth than the same amount of AmB formulated as AmBisome®. Apo-A-I-AmB bioactive agent delivery particles achieved 90% growth inhibition at 1 µg/ml, whereas this level of inhibition required 25 µg/ml AmBisome®.

Anti-fungal activity of ApoA-I-AmB particles and AmBisome® were also compared against two species of pathogenic fungi, *Candida albicans* (*C. albicans*) and *Aspergillus fumigatus* (*A. fumigatus*), in microtiter broth whole-cell assays. As a control, particles without AmB were also tested. The results are shown in Table 1.

TABLE 1

Amphotericin B Inhibition of Pathogenic Fungal Growth

| | $ED_{90}$ (µg/ml) | | |
|---|---|---|---|
| Organism | AmBisome | Delivery particles with AmB | Control particles without AmB |
| *Candida albicans* | 0.8 | 0.1 | No inhibition |
| *Aspergillus fumigatus* | 1.6 | 0.2 | No inhibition |

The results obtained revealed that AmB-containing bioactive agent delivery particles were effective against both pathogenic fungal species, at a lower concentration than AmBisome®. Control particles lacking AmB were not effective. AmB-containing bioactive agent delivery particles exhibited an $ED_{90}$ (concentration at which 90% growth inhibition is observed) for *C. albicans* at a concentration of 0.1 µg/ml, whereas 0.8 µg/ml AmBisome® was required to achieve the same level of growth inhibition. For *A. fumigatus*, AmB-containing bioactive agent delivery particles inhibited 90% of fungal growth at a concentration of 0.2 µg/ml, whereas 1.6 µg/ml AmBisome® was required to achieve the same effect.

In another experiment, AmB-containing bioactive agent delivery particles containing apolipophorin III as the lipid-binding polypeptide were compared with AmBisome® for their ability to inhibit growth of three species of pathogenic fungi, *C. albicans, A. fumigatus*, and *Cryptococcus neoformans* (*C. neoformans*). The data are shown in Table 2.

TABLE 2

Amphotericin B Inhibition of Pathogenic Fungal Growth

| | $ED_{90}$ (µg/ml) | | |
|---|---|---|---|
| Organism | AmBisome | Delivery particles with AmB | Control particles without AmB |
| *Candida albicans* | 0.4 | 0.03 | No inhibition |
| *Aspergillus fumigatus* | 2.5 | 0.1 | No inhibition |
| *Cryptococcus neoformans* | 0.31 | 0.06 | No inhibition |

AmB-containing bioactive agent delivery particles inhibited 90% of *C. albicans* growth at 0.03 µg/ml. A corresponding $ED_{90}$ of 0.4 µg/ml was obtained with AmBisome®. In the case of *A. fumigatus*, AmB-containing bioactive agent delivery particles inhibited 90% of fungal growth at 0.1 µg/ml, whereas a concentration of 2.5 µg/ml AmBisome® was required to achieve the same effect. In a similar manner, AmB-containing particles were effective at inhibiting *C. neoformans* growth at a five-fold lower AmB concentration than AmBisome®.

All samples tested were soluble in the RPMI media used for the experiments and no precipitation or interference was observed in any of the samples tested against any of the fungal species. These data suggest that a formulation of AmB in the bioactive agent delivery particles of the invention has more potent anti-fungal activity than a liposomal formulation.

Example 9

Incorporation of Camptothecin into Bioactive Agent Delivery Particles

Camptothecin-containing bioactive agent delivery particles were prepared as follows: A 7:3 molar ratio of DMPC:DMPG (5 mg total) was dispersed in buffer (20 mM sodium phosphate, pH 7.0) by vortexing for 1 minute to generate a dispersion of phospholipid bilayer vesicles. Ten microliters of a 10 mg/ml solution of camptothecin in DMSO was added to the phospholipid bilayer dispersion. Two mg of recombinant human apolipoprotein A-I (0.5 ml of a 4 mg/ml solution in 20 mM sodium phosphate, pH 7.0) was then added, and the sample was then subjected to sonication. The clarified sample was then centrifuged at 13,000×g for 3 minutes and the supernatant recovered and stored at 4° C.

Figure 11:
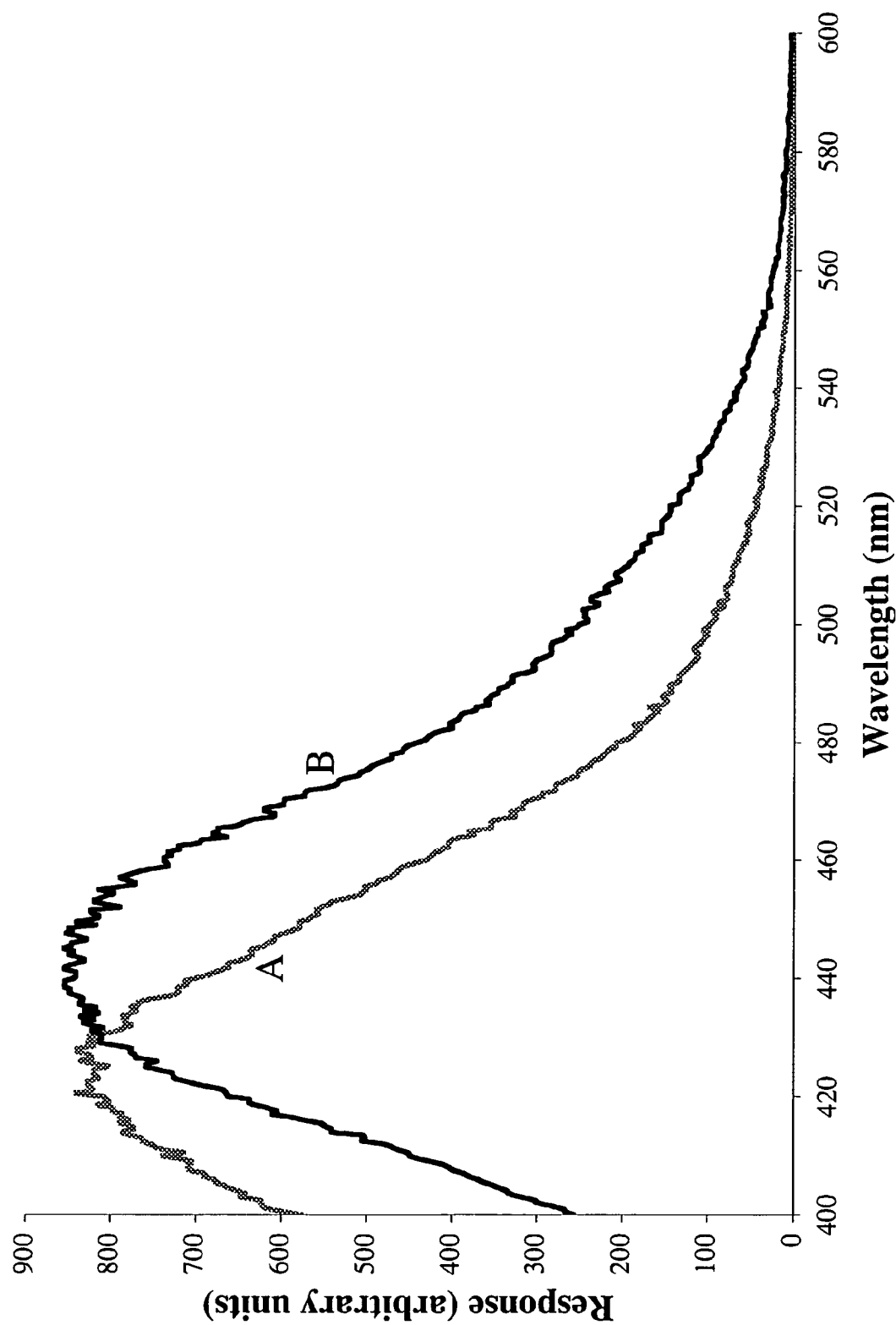
FIG. 11 shows fluorescence spectral comparison between camptothecin solubilized in SDS (FIG. 11A) and camptothecin-containing bioactive agent delivery particles (FIG. 11B), as described in Example 9.

A fluorescence spectrum of the camptothecin-containing particles, in comparison with sodium dodecyl sulfate (SDS) solubilized camptothecin, is shown in FIG. 11. Fluorescence measurements were obtained on a Perkin Elmer LS 50B luminescence spectrometer at an excitation wavelength of 360 nm with emission monitored from 400 to 600 nm. The blue shift in fluorescence emission maximum elicited by camptothecin in SDS micelles (FIG. 11A) compared to camptothecin incorporated into bioactive agent delivery particles (FIG. 11B) suggests that the drug localizes to a more hydrophobic environment in the micelles versus the delivery particles.

Example 10

Freeze Fracture Electron Microscopy of AmB-containing Bioactive Agent Delivery Particles A preparation of AmB-containing bioactive agent delivery particles was prepared for freeze fracture electron microscopy as follows: A sample of DMPC:DMPG (7:3 molar ratio) AmB bioactive agent delivery particles (3 mg/ml protein), prepared as in Example 6, was quenched using a sandwich technique, and liquid nitrogen cooled propane. The cryofixed sample was stored in liquid nitrogen for less than 2 hours prior to processing. The fracturing process was carried out in JOEL JED-900 freeze-etching equipment and the exposed fracture planes were shadowed with Pt for 30 seconds at an angle of 25-35 degrees, and with carbon for 35 seconds (2 kV/60-80 mA, $1 \times 10^{-5}$ Torr). The replicas produced in this way were cleaned with concentrated fuming $HNO_3$ for 24 hours followed by repeated agitation with fresh chloroform/methanol (1:1 by volume) at least 5 times. The replicas cleaned in this way were examined on a JOEL 100 CX or a Philips CM 10 electron microscope.

Figure 9:
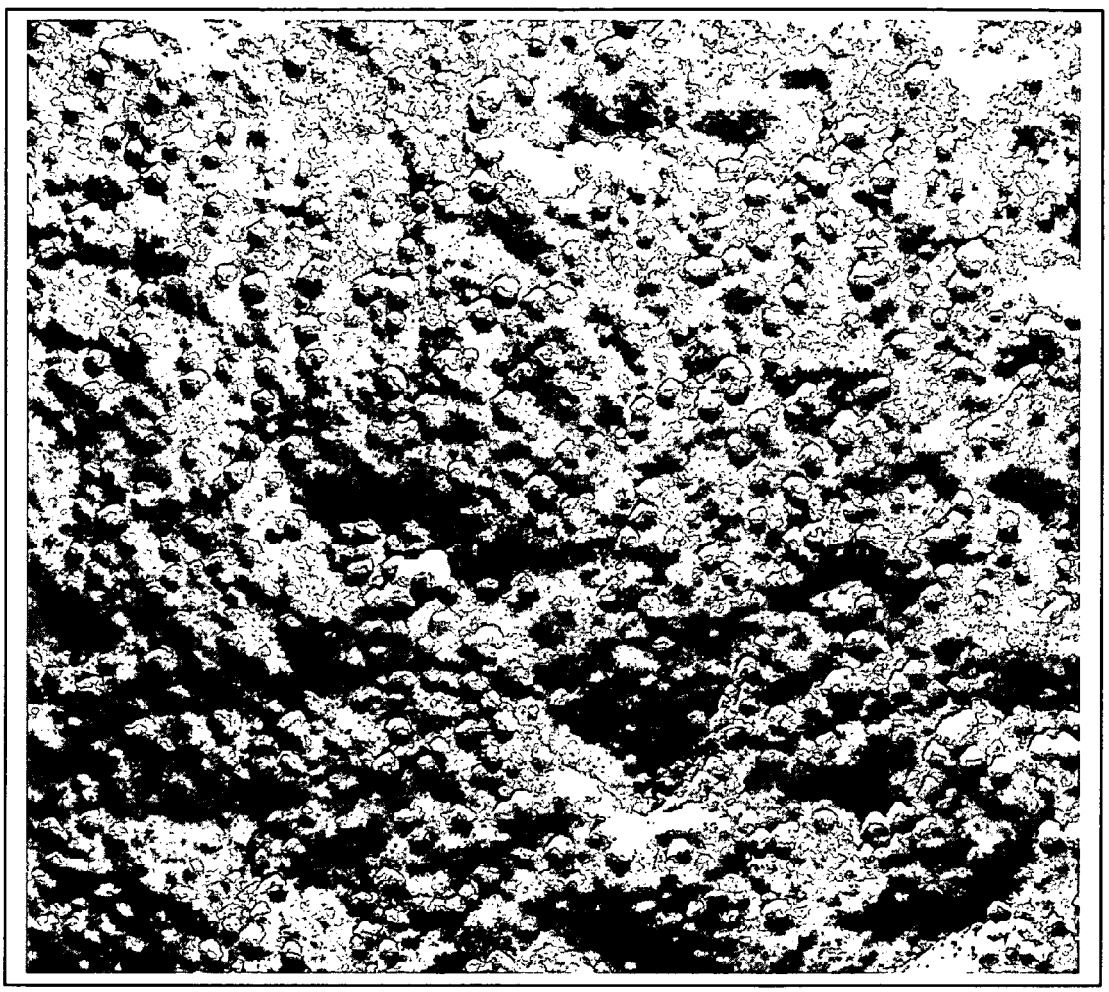
FIG. 9 is a freeze fracture electron micrograph of AmB-containing bioactive agent delivery particles, prepared as described in Example 10.

An electron micrograph obtained from freeze fracture of AmB-containing particles as described above is shown in FIG. 9. Electron micrographs taken from several freeze-fracture preparations indicate the presence of small protein-lipid complexes in high concentration. The apparent diameters range from about 20-60 nm with high frequency around 40 nm. The apparent diameter of particles as observed by freeze fracture electron microscopy is larger than values obtained by native pore limiting gradient gel electrophoresis. The difference may be due to the effect of sample handling or the staining procedure used to visualize the particles by electron microscopy.

The substantially spherical complexes do not display concave or convex fracture faces (shadow in front and behind the structure, respectively), as are characteristic for liposomes. Further, no evidence for micellar structures was observed.

Example 11

In Vivo Assessment of Anti-Fungal Activity of AmB-Containing Bioactive Agent Delivery Particles in Immunocompetent Mice In vivo anti-fungal activity of AmB-containing bioactive agent delivery particles is assessed as follows:

Animals

Six to eight-week-old female BALB/c mice (20-25 g) are housed and maintained under standard laboratory conditions.

Toxicity Study

Groups of three mice each receive a dose (e.g., 1, 2, 5, 10, or 15 mg/kg AmB) in AmB-containing bioactive agent delivery particles, or control particles without AmB, in saline buffered to pH 7.4 with 10 mM sodium phosphate. A single dose is administered as a 0.1 ml volume intraperitoneally. Preliminary studies have indicated that the bioactive agent delivery particles are fully soluble under these conditions.

Following injection, the mice are observed for any general reaction, for example, abnormal movement or posture, difficulty in breathing, ruffled fur, or inability to obtain food or drink. Observation for abnormality or mortality begins immediately after administration and continues twice daily for seven days. Body weight is recorded daily for the same period.

Blood is collected from mice prior to euthanization. The blood is assayed for liver enzymes such as lactate dehydrogenase to assess the degree of liver specific damage Efficacy of AmB-Containing Bioactive Agent Delivery Particles in Treatment of Systemic *cryptococcus*

The therapeutic range of AmB-containing particles is determined and compared with AmBisome® as follows:

A clinical isolate of *C. neoformans* that is susceptible to AmB is cultured and prepared as an inoculum for infection at a concentration of $2 \times 10^6$ conidia/ml. Each mouse receives an inoculum of $1 \times 10^5$ conidia in 0.05 ml of normal saline intracranially under general anesthesia.

Anti-fungal agents are administered intraperitoneally in 0.1 ml volumes daily for 5 days, starting 2 hours post-infection. The dosage of AmB used is determined based on the toxicity studies described above. One treatment group of mice receives AmBisome®, one treatment group receives AmB-containing bioactive agent delivery particles, and a control group receives no therapy.

Infected mice are monitored twice daily and any signs of illness or mortality is recorded for up to 28 days. Body weight is recorded daily for the same time period. Moribund animals that fail to move normally or take food or drink are euthanized. Based on the outcome of these studies, a second set of studies is performed to verify and reproduce the findings. The AmB dose employed, as well as the number of mice in the control and treatment groups, may be adjusted to reflect knowledge gained from the previous experiment.

Determination of Tissue Fungal Burden

Mice are sacrificed one day after the last day of treatment. The kidneys and brains are removed aseptically and weighed. Tissues are homogenized and serially diluted in normal saline. The homogenates are cultured for 48 hours on PDA (potato dextrose agar) plates to determine the colony forming units (CFU). Fungal burden of CFU/gram of tissue is determined.

Statistical Analyses

Differences in survival and mean CFUs in kidney or brain are compared using statistical tests as appropriate.

Pharmacokinetic Study

Blood, liver, kidney, ling, and cerebrospinal fluid samples are collected from infected mice at time points of 10 minutes, 2, 8, and 24 hours after intravenous injection of AmB bioactive agent delivery particles or AmBisome® at 0.8 and 2.0 mg/kg doses. While mice are under general anesthesia, whole blood is collected from axillary vessels. A thoracotomoy is performed, and tissue samples perfused with normal saline and then removed surgically. Tissues are homogenized with methanol containing 1-amino-4-nitronaphthalene. Serum and the supernatants of tissue homogenates are preserved until analysis. The concentration of AmB in each sample is determined by high-performance liquid chromatography (HPLC), as described in Granich et al. (1986) *Antimicrob. Agents Chemother.* 29:584-88. Briefly, serum samples (0.1 ml) are combined with 1.0 ml methanol containing 1.0 mg of an internal standard, 1-amino-4-nitronaphthalene, per ml and mixed by vortexing. After centrifugation, the supernatant is dried under reduced pressure followed by redissolving with 0.2 ml of methanol for injection onto a HPLC column ($C_{18}$ reverse phase). Weighed wet tissue samples are homogenized in 10 volumes of methanol containing 5.0 mg internal standard per ml with a glass homogenizer and centrifuged. The mobile phase is a mixture of acetonitrile and 10 mM sodium acetate buffer (pH 4.0; 11:17 (vol/vol)), at a flow rate of 1.0 ml/min. The concentration of AmB is determined by the ratio of the peak height of AmB to that of the internal standard.

Example 12

Targeting of Camptothecin-Containing Bioactive Agent Delivery Particles to Tumor Cells Bioactive agent delivery agent particles are prepared with a VIP targeting moiety attached to the lipid binding polypeptide component.

The lipid binding polypeptide component of the camptothecin-containing particles may be generated in recombinant form in *Escherichia coli* (*E. coli*) that have been transformed with a plasmid vector harboring the coding sequence of the lipid binding polypeptide. For example, recombinant human ApoA-I may be employed. *E. coli* cells harboring an ApoA-I expression plasmid are cultured in media at 37° C. When the optical density of the culture at 600 nm reaches 0.6, ApoA-I synthesis is induced by the addition of isopropylthiogalactoside (0.5 mM final concentration). After a further 3 hours of culture, the bacteria are pelleted by centrifugation and disrupted by sonication. The cell lysate is centrifuged at 20,000×g for 30 min at 4° C. and apoA-I isolated from the supernatant fraction.

A recombinant lipid binding polypeptide chimera is produced by engineering ApoA-I to include an N-terminal and/or C-terminal peptide extension that corresponds to the 28 amino acid neuropeptide, vasoactive intestinal peptide (VIP). ApoA-I-VIP chimeras may be employed to create bioactive agent delivery particles comprised of phospholipid, camptothecin and ApooA-I-VIP chimera.

For example, an ApoA-I-VIP chimera may be constructed by synthesizing complementary oligonucleotide primers corresponding to the coding sequence of the VIP sequence possessing terminal Hind III and Xba I sites. The oligonucleotides (~100 base pairs) are annealed to generate double stranded DNA with the desired "sticky ends" and subcloned into the ApoA-I coding sequence-containing plasmid vector that has appropriately placed Hind III and Xba I restriction enzyme sites. Following ligation, transformation and screening for a positive chimera construct, the plasmid DNA is isolated and subject to automated dideoxy chain termination sequence analysis. Following confirmation that the sequence corresponds to that predicted for the desired chimera, production of recombinant ApoA-I-VIP chimera is performed in *E. Coli*, as described above for wild type ApoA-I. Purified recombinant chimera is then evaluated by gel electrophoresis, mass spectrometry and for its ability to generate bioactive agent delivery particles of the invention in a manner similar to wild type ApoA-I, as described in Example 8.

ApoA-I-VIP chimera-camptothecin-containing bioactive agent delivery particles may be used in breast cancer cell growth inhibition studies to measure the extent of lipid particle targeting. For example, the human breast cancer cell line MCF-7 is obtained from the American Type Culture Collection and maintained at 37° C. in a humidified 5% $CO_2$ incubator as monolayer cultures in modified Eagle's media supplemented with 10% fetal bovine serum and the antibiotics penicillin and streptomycin. Isolated wild type ApoA-I or ApoA-I-VIP chimera is radioiodinated and incorporated into camptothecin-containing bioactive agent delivery particles of the invention and incubated with the cells. Cell-associated radioactivity is determined after incubation of labeled camptothecin-containing bioactive agent delivery particles with cultured MCF-7 cells at 4° C. The ability of VIP to compete for binding of ApoA-I-VIP chimera or bioactive agent delivery particle-associated ApoA-I-VIP chimera to MCF cells is determined in competition binding assays. Cell binding data is evaluated by Scatchard analysis. The extent of MCF-7 cell internalization of ApoA-I-VIP chimera bioactive agent delivery particles is evaluated in incubations with radioiodinated ApoA-I-VIP chimera-containing bioactive agent delivery particles at 37° C. After incubation and washing, trichloroacetic acid soluble radioactivity is determined, providing a measure of lipid binding polypeptide degradation.

Growth inhibition and cytotoxicity studies with different bioactive agent delivery particles are assessed by clonogenic assay. Exponentially growing cells are resuspended in media and cell number determined using an electronic counter. Alternatively, camptothecin-ApoA-I-VIP chimera bioactive agent delivery particle inhibition of MCF-7 clonal growth may be evaluated on the basis of reduced $^{35}$S-methionine uptake. Aliquots of cells are inoculated in triplicate into culture dishes. After incubation, specific lipid particles are added from a stock solution to the dishes to achieve final concentrations of 0, 0.1, 1, 5, 10, 50, 100, and 250 nM camptothecin. After specific time intervals ranging from 0 to 72 hours, medium is removed by aspiration and fresh medium added. The percentage survival at each drug concentration with different exposure times is determined from the ratio of the number of Trypan Blue excluding cells and compared to results obtained with control particles lacking camptothecin.

Although the foregoing invention has been described in some detail by way of illustration and examples for purposes of clarity of understanding, it will be apparent to those skilled in the art that certain changes and modifications may be practiced without departing from the spirit and scope of the invention. Therefore, the description should not be construed as limiting the scope of the invention, which is delineated by the appended claims.

All publications, patents, and patent applications cited herein are hereby incorporated by reference in their entirety for all purposes and to the same extent as if each individual publication, patent, or patent application were specifically and individually indicated to be so incorporated by reference.

We claim:

1. A bioactive agent delivery particle consisting essentially of at least one lipid binding polypeptide, a lipid bilayer, and one or more bioactive agents comprising at least one hydrophobic region wherein said bioactive agent is a non-polypeptide selected from the group consisting of antimicrobials, neurotransmitters, radiolabels, fluorescent compounds, antimetabolic agents, anesthetics, anticancer agents, anti-inflammatory agents, pesticides, insecticides, herbicides, all-trans retinoic acid, lipopolysaccharide, Vitamin E, and photosensitizing agents used in photodynamic therapy,
    wherein the lipid bilayer comprises at least one phospholipid and the interior of the lipid bilayer comprises a hydrophobic region and the one or more bioactive agents is incorporated into the hydrophobic region of the lipid bilayer, and
    wherein the particle
        does not comprise an aqueous core,
        is disc-shaped with the hydrophobic edge of the lipid bilayer circumscribed by the lipid binding polypeptide at the periphery of the particle and remains disc shaped in aqueous solution, and
    wherein said lipid binding polypeptide comprises a class A amphipathic α-helix structural motif and/or a β-sheet motif and is selected from the group consisting of apolipoproteins and chimeric apolipoproteins.

2. A bioactive agent delivery particle according to claim 1, wherein the disc shaped particle comprises a diameter from about 7 to about 29 nm.

3. A bioactive agent delivery particle according to claim 1, wherein the bioactive agent is amphotericin B.

4. A bio active agent delivery particle according to claim 1, wherein the bioactive agent is camptothecin.

5. A bioactive agent delivery particle according to claim 1, wherein the lipid binding polypeptide is an apolipoprotein.

6. A bioactive agent delivery particle according to claim 5, wherein the apolipoprotein is an exchangeable apolipoprotein.

7. A bioactive agent delivery particle according to claim 6, wherein the apolipoprotein is human apolipoprotein A-I.

8. A bioactive agent delivery particle according to claim 1, wherein the lipid binding polypeptide is a chimeric apolipoprotein that comprises a functional moiety.

9. A bioactive agent delivery particle according to claim 8, wherein the functional moiety is a targeting moiety.

10. A bioactive agent delivery particle according to claim 8, wherein the functional moiety comprises biological activity.

11. A bioactive agent delivery particle according to claim 5, wherein the apolipoprotein has been modified to increase stability of the particle.

12. A bioactive agent delivery particle according to claim 11, wherein the modification comprises introduction of cysteine residues to form intermolecular or intramolecular disulfide bonds.

13. A bioactive agent delivery particle according to claim 1, wherein the phospholipids comprise dimyristoylphosphatidylcholine (DMPC) and dimyristoylphosphatidylglycerol (DMPG).

14. A pharmaceutical composition for delivery of a bioactive agent to an individual, comprising a bioactive agent delivery particle according to claim 1 and a pharmaceutically acceptable carrier.

15. A pharmaceutical composition according to claim 14, wherein the composition is formulated for controlled release.

16. A method for administering a bioactive agent to an individual, comprising administering the pharmaceutical composition of claim 14 to the individual.

17. A method according to claim 16, wherein said pharmaceutical composition comprises a therapeutically effective amount of the bioactive agent.

18. A method according to claim 17, wherein the bioactive agent is amphotericin B.

19. A method according to claim 17, wherein the bioactive agent is camptothecin.

20. A method according to claim 16, wherein administration is parenteral.

21. A method according to claim 20, wherein said parenteral administration is selected from the group consisting of intravenous, intramuscular, transmucosal, and intrathecal.

22. A method according to claim 16, wherein the composition is administered as an aerosol.

23. A method according to claim 16, wherein the composition is formulated for controlled release.

24. A kit comprising a pharmaceutical composition according to claim 14 and instructions for use in a method for administering a bioactive agent to an individual.

25. A bioactive agent delivery particle according to claim 1, wherein the bioactive agent is an antimicrobial, a pesticide, or a herbicide.

26. A bioactive agent delivery particle according to claim 25, wherein the antimicrobial is an antifungal.

27. A bioactive agent delivery particle according to claim 25, wherein the bioactive agent is an insecticide.

28. A bioactive agent delivery particle according to claim 1, wherein the bioactive agent is nystatin.

29. A bioactive agent delivery particle according to claim 1, wherein the bioactive agent is an anticancer agent.

30. A bioactive agent delivery particle according to claim 1, wherein the bioactive agent comprises all-trans retinoic acid, or Vitamin E.

31. A bioactive agent delivery particle according to claim 1, wherein the lipid binding polypeptide is a peptide.

32. A bioactive agent delivery particle according to claim 31, wherein the lipid binding polypeptide is an amphipathic peptide.

33. A bioactive agent delivery particle according to claim 5, wherein the apolipoprotein is apolipoprotein E.

34. A bioactive agent delivery particle according to claim 33, wherein the apolipoprotein is the N-terminal domain of apolipoprotein E.

35. A bioactive agent delivery particle according to claim 1, wherein the phospholipids comprise dipalmitoylphosphatidylcholine (DPPC) or egg phosphatidylcholine.

36. A pharmaceutical composition, comprising a bioactive agent delivery particle according to claim 35 and a pharmaceutically acceptable carrier.

37. A composition for delivery of a bioactive agent to an individual, comprising a bioactive agent delivery particle of claim 1 and a carrier.

38. A composition according to claim 37, wherein the individual is a plant or insect.

39. A composition according to claim 37, wherein the bioactive agent is an antimicrobial, a pesticide, or a herbicide.

40. A composition according to claim 14, wherein the composition is formulated for topical administration.

41. The method according to claim 16, wherein administration is topical.

42. The method of claim 16, wherein the individual is a plant.

43. The bioactive agent delivery particle according to claim 1, wherein the apolipoprotein is selected from the group consisting of apolipoprotein A-I (ApoA-I), apolipoprotein E (ApoE), apolipoprotein E3 (ApoE3), apolipophorin III (ApoIII), apolipoprotein A-IV (ApoA-IV), apolipoprotein A-V (ApoA-V), apolipoprotein C-I (ApoC-I), apolipoprotein C-II (ApoC-II), apolipoprotein C-III (ApoC-III), apolipoprotein D (ApoD), apolipoprotein A-II (ApoA-II), apolipoprotein B-100 (ApoB-100), apolipoprotein J (ApoJ), apolipoprotein H (ApoH), and natural variants, analogs, fragments, isoforms, or chimeric forms thereof.

44. The bioactive agent delivery particle according to claim 1, wherein the lipid binding polypeptide is an apolipoprotein natural variant, isoform, fragment or analog.

45. The bioactive agent delivery particle of claim 31, wherein the peptide is a synthetic peptide.

46. The bioactive agent delivery particle according to claim 1, wherein the apolipoprotein is the C-terminal or N-terminal domain of apolipoprotein E3 or isoform thereof.

* * * * *

UNITED STATES PATENT AND TRADEMARK OFFICE
CERTIFICATE OF CORRECTION

PATENT NO. : 7,824,709 B2  Page 1 of 1
APPLICATION NO. : 10/778640
DATED : November 2, 2010
INVENTOR(S) : Robert O. Ryan et al.

It is certified that error appears in the above-identified patent and that said Letters Patent is hereby corrected as shown below:

At column 10, line number 22, please replace "-NH2" with --$NH_2$--

At column 10, line number 53, please replace "Amheim" with --Arnheim--

At column 15, line number 51, please replace *"Leishmania* spp." with --*Leishmania spp.*--

At column 28, claim 4, line 6, please replace "bio active" with --bioactive--

Signed and Sealed this
Eighth Day of March, 2011

David J. Kappos
*Director of the United States Patent and Trademark Office*

UNITED STATES PATENT AND TRADEMARK OFFICE
CERTIFICATE OF CORRECTION

| | | |
|---|---|---|
| PATENT NO. | : 7,824,709 B2 | Page 1 of 1 |
| APPLICATION NO. | : 10/778640 | |
| DATED | : November 2, 2010 | |
| INVENTOR(S) | : Ryan et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1125 days.

Signed and Sealed this
Twenty-sixth Day of April, 2011

David J. Kappos
*Director of the United States Patent and Trademark Office*

UNITED STATES PATENT AND TRADEMARK OFFICE
CERTIFICATE OF CORRECTION

| | | |
|---|---|---|
| PATENT NO. | : 7,824,709 B2 | Page 1 of 1 |
| APPLICATION NO. | : 10/778640 | |
| DATED | : November 2, 2010 | |
| INVENTOR(S) | : Robert O. Ryan et al. | |

It is certified that error appears in the above-identified patent and that said Letters Patent is hereby corrected as shown below:

In the Specification:

Col. 1, lines 17-19, please replace:

"This invention was made in part during work supported by grant no. HL064159 from the National Institutes of Health. The government has certain rights in the invention."

with:

--This invention was made with government support under federal grant no. HL064159 from the National Institutes of Health. The government has certain rights in this invention.--

Signed and Sealed this
Thirteenth Day of May, 2014

Michelle K. Lee
*Deputy Director of the United States Patent and Trademark Office*